United States Patent [19]

Tomita

[11] Patent Number: 5,316,005
[45] Date of Patent: May 31, 1994

[54] APPARATUS FOR DETECTING AND DISPLAYING BLOOD CICULATORY INFORMATION

[76] Inventor: Mitsuei Tomita, 407 Yamanote Villa Porte, 109 Yamanote-Cho, Naka-Ku, Yokohama 231, Japan

[21] Appl. No.: 809,499
[22] PCT Filed: May 17, 1990
[86] PCT No.: PCT/JP90/00623
  § 371 Date: Jan. 13, 1992
  § 102(e) Date: Jan. 13, 1992
[87] PCT Pub. No.: WO91/17699
  PCT Pub. Date: Nov. 28, 1991
[51] Int. Cl.$^5$ ............................................. A61B 5/02
[52] U.S. Cl. .................... 128/680; 128/687; 128/686
[58] Field of Search ............... 128/677–686; 364/413.03

[56] References Cited

U.S. PATENT DOCUMENTS

| | | | |
|---|---|---|---|
| 4,144,879 | 3/1979 | Nakayama et al. | 128/680 |
| 4,417,587 | 11/1983 | Ichinomiya et al. | 128/682 |
| 4,664,126 | 5/1987 | Link | 128/680 |
| 4,949,710 | 8/1990 | Dorsett et al. | 128/680 |
| 5,069,219 | 12/1991 | Knoblich | 128/686 |

*Primary Examiner*—Lee S. Cohen
*Assistant Examiner*—Robert L. Nasser, Jr.
*Attorney, Agent, or Firm*—Ladas & Parry

[57] ABSTRACT

A cuff (200; 500) is put around an upper arm, and the blood flow of the upper arm is shut by a blood flow shutting bag (210; 520). A sound wave sensor (110) and a pressure sensor (120) are disposed in a rear detecting bags (230; 530) downstream of the blood flow shutting bag to detect pulse waves and Korotkoff sounds. The reference internal pressure in the cuff is controlled by an air pump and a leak valve controlled by a CPU (130; 430; 640). By monitoring the Korotkoff sounds or the pulse waves, the reference internal pressure of the cuff can be maintained at a diastolic pressure DP. A pulse wave obtained at this pressure on an upper arm is approximate to an aortic wave. This approximate aortic wave is displayed together with the Korotkoff sounds and its envelope, and an output indicative of blood circulation trouble information of the circulation system is obtained.

4 Claims, 26 Drawing Sheets

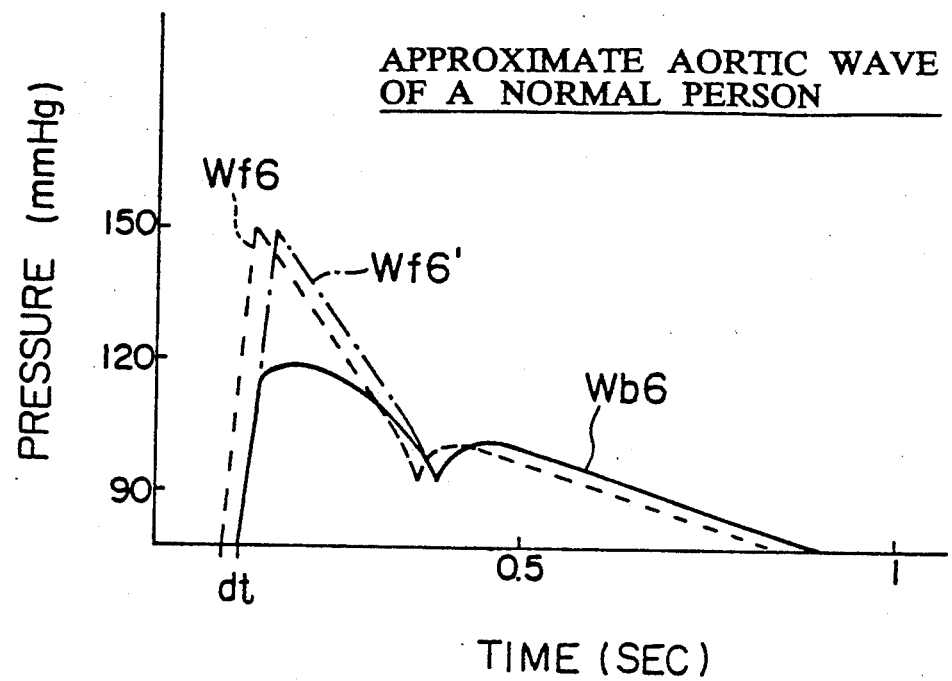
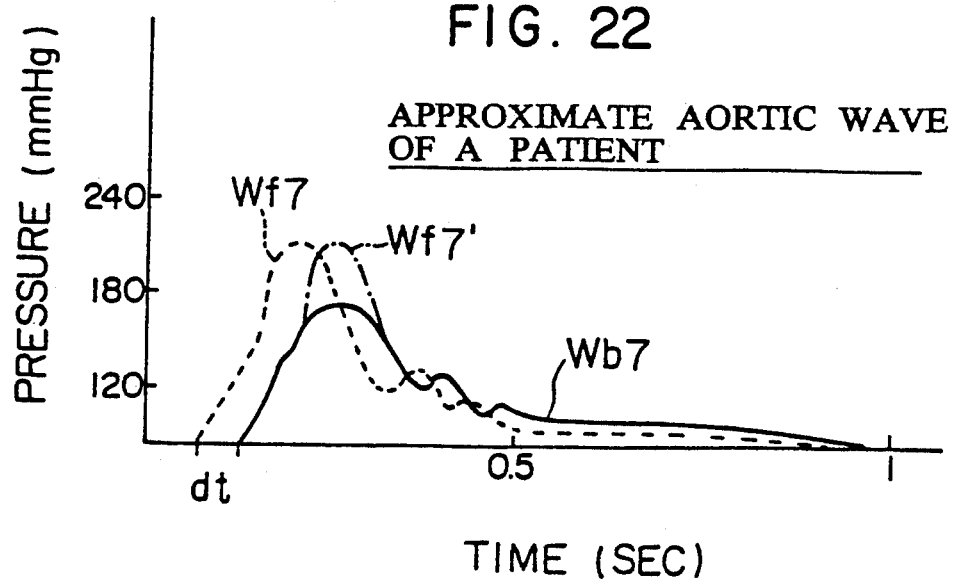

-R2  -R1  N  -L1  -L2

APPARATUS FOR DETECTING AND DISPLAYING BLOOD CICULATORY INFORMATION

TECHNICAL FIELD

This invention relates to an apparatus for detecting and displaying blood circulatory information, specifically a device for detecting pulse waves non invasively using a cuff, obtaining blood circulatory information based on the detected pulses, and displaying the information in a form suitable for diagnoses.

BACKGROUND ART

The diagnosis of circulatory organ diseases requires blood pressure measurement and analysis of pulse waves. Especially the analysis of aortic waves near the heart is very effective to the diagnosis of the heart diseases. The method for measuring the aortic wave is classified in invasive method and non invasive method. As the invasive method, conventionally blood vessel catheter measurement method has been used. In this method a catheter is inserted into an artery up to a part to be measured so as to directly measure the pulse waves there. On the other hand, as the non invasive one, methods using ultrasonic waves and nuclear magnetic resonance have been developed and are practically used. Arterial sounds obtained under a pressure of a cuff, which are known as Korotkoff sounds, are considered to contain precious information for the diagnosis of the circulatory organ diseases.

But the above mentioned invasive blood vessel catheter measurement method is a bulky method including the insertion of a catheter into an artery. Unpreferably this method physically and mentally burdens patients. On the other hand, the non invasive method less burdens patients but has a problem that pulse waves cannot be measured together with specific blood pressure values. That is, what can be obtained by non invasive method is only forms of pulse waves. Their blood pressure values cannot be concurrently measured. Their blood pressure values have to be measured by other different methods. The diagnoses of heart disease patients essentially require the measurement of pulse waves concurrent with the measurement of their specific blood pressure values. The pulse waves alone obtained by the conventional non invasive method have been insufficient to the diagnoses of heart diseases.

In the above described conventional pulse wave detecting apparatus, one pulse wave is displayed merely separately. To the diagnoses of heart diseases it is one important factor to know transient changes of a pulse wave. But the conventional apparatus have found it difficult to analyze transient changes of a pulse wave.

There is a problem that, based on measurement results of the conventional apparatuses, synthetic diagnoses cannot be made, using pulse waves, blood pressures, and arterial sounds. The synthetic understanding of the three factors, pulse waves, blood pressures and arteiral sounds, are very important to the diagnoses of circulatory organ diseases.

The conventional apparatus cannot visually display a state of the blood circulation throughout the body of a patient. This results in much time and labor.

DISCLOSURE OF THE INVENTION

A first object of this invention is to provide a pulse wave detecting apparatus which enables non invasively both pulse waves and blood pressures to be concurrently detected.

A second object of this invention is to provide a pulse wave change detecting apparatus which can provide transient changes of pulse waves in a form which can be easily understood.

A third object of this invention is to provide a pulse-wave/arterial-sound composite recording apparatus which can compositely record pulse waves, blood pressures, arterial sounds in a form which allows synthetic judgements to be visually made.

A fourth object of this invention is to provide a blood circulation information display apparatus which can display a state of the blood circulation throughout the body of a patient in a form which can be visually understood.

(1) To achieve the above described first object, a pulse wave detecting apparatus according to a first feature of the present invention comprises:

a cuff including a blood flow shutting bag for shutting blood flow of an upper arm, and a detection bag for detecting a pulse which has cleared the blood flow shutting bag;

a pressure sensor for detecting a pressure change generated in the detection bag;

a pressure control unit which functions to maintain a reference internal pressure of the blood flow shutting bag and of the detection bag at a set value; and a pulse wave output unit for outputting as data indicative of the pulse wave the pressure change provided by the pressure sensor while the reference internal pressure is being maintained at the set value.

(2) To achieve the above described first object, a pulse wave detecting apparatus according to a second feature of the present invention comprises:

a cuff including a blood flow shutting bag for shutting blood flow of an upper arm, and a detection bag for detecting a pulse which has cleared the blood flow shutting bag;

a sound wave sensor for detecting a Korotkoff sound generated by putting around the cuff;

a pressure sensor for detecting a pressure change generated in the detection bag;

a pressure control unit which functions to gradually decrease a reference internal pressure of the blood flow shutting bag and of the detection bag from a high value sufficient for the blood flow shutting and, when a sound volume of the Korotkoff sound detected by the sound wave sensor reaches a set value, to maintain the reference internal pressure at a set value; and a pulse wave output unit for outputting as data indicative of the pulse wave the pressure change provided by said pressure sensor while the reference internal pressure is being maintained at the set value.

(3) In the pulse wave detecting apparatus according to the above described second feature, a third feature of the present invention is characterized in that:

when a sound volume of the Korotkoff sound is maintained substantially at the set value irrespective of decrease of the reference internal pressure, reversely the reference internal pressure is increased, and when the sound volume of the Korotkoff sound becomes larger to some extent than the set value, the reference internal pressure is maintained.

(4) To achieve the above described first object of this invention, a pulse wave detecting apparatus according to a fourth feature of the present invention comprises:

a cuff including a blood flow shutting bag for shutting blood flow of an upper arm, a forward detection bag for detecting a pulse wave going to the blood flow shutting bag, and a rear detection bag for detecting a pulse wave which has passed the blood flow shutting bag;

a forward sensor for detecting as a forward pulse wave a pressure change generated in the forward detection bag;

a rear sensor for detecting as a rear pulse wave a pressure change generated in the rear detection bag, later by a delay time from a time of a detection of the forward pulse wave;

agreement judging means for multiplexing the forward pulse wave on the rear pulse wave with the delay time to judge whether or not lower waveforms of both pulse waves agree with each other with a set precision;

a pressure control unit which functions to gradually decrease a reference internal pressure of the blood flow shutting bag and of the respective detection bags from a high value sufficient for the blood flow shutting and, when the agreement judging means indicates an agreement, to maintain the reference internal pressure at a set value; and a pulse wave output unit for outputting as an approximate aortic wave near a heart the rear pulse wave provided by the rear sensor while the reference internal pressure is being maintained at the set value.

(5) In the pulse wave detecting apparatus according to the above described fourth feature, a fifth feature of the present invention is characterized in that:

the agreement judging means multiplexes the forward pulse wave and the rear pulse wave so that rising parts of the former and of the latter agree with each other, and judges whether or not waveforms of parts of both pulse waves below dicroticnotch pressures thereof agree with each other with a set precision.

(6) In the pulse wave detecting apparatus according to the above described fourth feature, a cuff according to a sixth feature of the present invention characterized in that:

a capacity of the forward detection bag and that of the rear detection bag are designed to be smaller than that of the blood flow shutting bag, and the blood flow shutting bag and the rear detection bag are communicated with a communication passage.

(7) To achieve the above described second object, a pulse wave detecting apparatus according to a seventh feature of the present invention comprises:

a pressure sensor for detecting as pressure changes a pulse wave generated in a living body;

a memory for storing waveforms of a plurality of pressure changes consecutively detected by the pressure sensor;

waveform multiplexing means for multiplexing the waveforms stored in the memory with rising times of the respective waveforms agreed with one another; and output means for outputting the waveforms multiplexed by the waveform multiplexing means.

(8) To achieve the above described second object, a pulse wave detecting apparatus according to an eighth feature of the present invention comprises:

a cuff including a blood flow shutting bag for shutting blood flow of an upper arm, and a detection bag for detecting a pulse which has cleared the blood flow shutting bag;

a sound wave sensor for detecting a Korotkoff sound generated by putting around the cuff;

a pressure sensor for detecting a pressure change generated in the detection bag;

a pressure control unit which functions to gradually decrease a reference internal pressure of the blood flow shutting bag and of the detection bag from a high value sufficient for the blood flow shutting and, when a sound volume of the Korotkoff sound detected by the sound sensor reaches a set value, to maintain the reference internal pressure at a set value;

a memory for storing a set number of waveforms of pressure changes consecutively provided by the pressure sensor while the reference internal pressure is being maintained at a set value;

waveforms multiplexing means for multiplexing the waveforms stored in the memory with rising times of the respective waveforms agreed with one another; and output means for outputting the waveforms multiplexed by the waveforms multiplexing means.

(9) To achieve the above described third object, a pulse-wave/arterial-sound composite recording apparatus according to a ninth feature of the present invention comprises:

a pulse wave detecting means for detecting a pulse wave generated in a living body;

a sound wave detecting unit for detecting a Korotkoff sound generated by pressing the living body by a cuff, changing a cuffing pressure, and recording a waveform of the Korotkoff sound along a pressure axis;

high pressure period display means for applying a pressure axis between a systolic pressure SP of the Korotkoff sound waveform recorded by the sound wave detecting unit and a dicroticnotch pressure DNP thereof linearly to a time axis between a time point T0 where the pulse wave detected by the pulse wave detecting unit rises and a time point T1 where a dicroticnotch thereof appears, whereby the pulse wave and the Korotkoff sound waveform are displayed on a same time axis; and low pressure period display means for applying a pressure axis between the dicroticnotch pressure DNP of the Korotkoff sound waveform recorded by the sound wave detecting unit and a diastolic pressure DP thereof linearly to a time axis between the time point T1 where the dicroticnotch of the pulse wave detected by the pulse wave detecting unit appears and a time point T2 where the pulse wave reaches a diastolic pressure DP, whereby the pulse wave and the Korotkoff sound waveform are displayed on a same time axis.

(10) In a pulse-wave/arterial-sound composite recording apparatus according to the ninth feature, a tenth feature of the present invention is characterized in that:

the high pressure period display means has a function of displaying standard lines indicative of positions where the time axis between the time points T0 and T1 are trisected, and the low pressure period display means has a function of displaying standard lines indicative of positions where the time axis between the time points T1 and T2 are bisected.

(11) In a pulse-wave/arterial-sound composite recording apparatus according to the ninth feature, an eleventh feature of the present invention is characterized in that:

the high pressure period display means and the low pressure period display means have a function of displaying a standard envelope of the Korotkoff sound waveform.

(12) In a pulse-wave/arterial-sound composite recording apparatus according to the ninth feature, a twelfth feature of the present invention is characterized in that:

on the time axis following the time point T2 there is further provided a third period display part for displaying the Korotokoff sound waveform below the diastolic pressure DP.

(13) In a pulse-wave/arterial-sound composite recording apparatus according to the above described ninth feature, a thirteenth feature of the present invention is characterized in that:

the high pressure period display means and the low pressure display means have a function of displaying a first detection result obtained by putting a cuff around a right arm, and a second detection result obtained by putting a cuff around a left arm symmetrically to each other with respect to a line along the time axis.

(14) To achieve the above described third object, a pulse-wave/arterial-sound composite recording apparatus according to a fourteenth feature of the present invention comprises:

a cuff including a blood flow shutting bag for shutting blood flow of an upper arm, and a detection bag for detecting a pulse which has cleared the blood flow shutting bag;

a sound wave sensor for detecting a Korotkoff sound generated by putting around the cuff;

a pressure sensor for detecting a pressure change generated in the detection bag;

a pressure control unit which functions to gradually decrease a reference internal pressure of the blood flow shutting bag and of the detection bag from a high value sufficient for the blood flow shutting and, when a sound volume of the Korotkoff sound detected by the sound wave sensor reaches a set value, to maintain the reference internal pressure at a set value;

a memory for storing a waveform of the Korotkoff sound detected by the sound wave sensor while the reference internal pressure is being decreased by the pressure control unit, together with reference internal pressure values at the detection;

means for obtaining an average pulse wave by averaging pressure changes consecutively supplied by the pressure sensor while the reference internal pressure is being maintained at the set value;

means for recognizing a systolic pressure SP of the average pulse wave, which is a maximum value thereof, a diastolic pressure DP, which is a minimum value thereof, and a dicroticnotch pressure DNP at a dicroticnotch thereof;

high pressure period display means for applying a pressure axis between the systolic pressure SP of the Korotkoff sound waveform stored in the memory and the dicroticnotch pressure DNP thereof linearly to a time axis between a time point T0 where the average pulse wave rises and a time point T1 where the dicroticnotch appears, whereby the pulse wave and the Korotkoff sound waveform are displayed on a same time axis; and low pressure period display means for applying a pressure axis between the dicroticnotch pressure DNP of the Korotkoff sound waveform stored in the memory and the diastolic pressure DP linearly to a time axis between the time point T1 where the discroticnotch of the pulse wave detected by the pulse wave detecting unit appears and a time point T2 where the pulse wave reaches the diastolic pressure DP, whereby the pulse wave and the Korotkoff sound waveform are displayed on a same time axis.

(15) To achieve the above described fourth object, a blood circulatory information display apparatus according to a fifteenth feature of the present invention comprises:

a pulse wave detecting unit for detecting a pulse wave generated in a living body;

a sound wave detecting unit for detecting a Korotkoff sound generated by pressing the living body by a cuff, changing a cuffing pressure, and recording a waveform of the Korotkoff sound along a pressure axis;

high pressure period superposing means for applying a pressure axis between a systolic pressure SP of the Korotkoff sound waveform recorded by the sound wave detecting unit to a dicroticnotch pressure DNP thereof linearly and a time axis between a time point T0 where the pulse wave detected by the pulse wave detecting unit rises and a time point T1 where a dicroticnotch thereof appears, whereby the pulse wave and the Korotkoff sound waveform are superposed on a graph with a time axis in common;

low pressure period superposing means for applying a pressure axis between the dicroticnotch pressure DNP of the Korotkoff sound waveform recorded by the sound wave detecting unit and a diastolic pressure DP thereof linearly to a time axis between the time point T1 where the dicroticnotch of the pulse wave detected by the pulse wave detecting unit appears and a time point T2 where the pulse wave reaches a diastolic pressure DP, whereby the pulse wave and the Korotkoff sound waveform are superposed on the graph; and a display unit for giving a first envelope connecting points at maximum peaks of the respective Korotkoff sound waves on the graph and second envelope connecting points at second maximum peaks of the respective Korotkoff sound waves on the graph, and displaying the pulse wave detected by the pulse wave detection unit, the first envelope and the second envelope on the graph.

(16) To achieve the above described fourth object, a blood circulatory information display apparatus according to a sixteenth feature of the present invention comprises:

a right sound wave detecting unit for detecting a Korotkoff sound generated by pressing a right arm of a human body with a cuff, changing a cuffing pressure, and recording a waveform of the Korotkoff sound on a pressure axis;

a left sound wave detecting unit for detecting a Korotkoff sound generated by pressing a left arm of the human body with the cuff, changing a cuffing pressure, and recording a waveform of the Korotkoff sound on a pressure axis; and icon displaying means for displaying a first icon indicative of a reference position, comparing the detected waveform supplied by the right sound wave detecting unit with a set reference, thus to display, in accordance with an interval between the two, a second icon at a position distant from the first icon, comparing the detected waveform supplied by the left sound wave detecting unit with a set reference to display, in accordance with an interval between the two, a third icon distant from the first icon on an opposite side to the second icon.

(17) To achieve the above described fourth object, a blood circulatory information display apparatus according to a seventeenth feature of the present invention comprises:

a pulse wave detecting unit for detecting a pulse wave generated in a human body;

a sound wave detecting unit for detecting a Korotkoff sound generated by pressing the human body with a cuff, changing a cuffing pressure, and recording a waveform of the Korotkoff sound along a pressure axis;

high pressure period superposing means for applying a pressure axis between a systolic pressure SP of the Korotkoff sound waveform recorded by the sound wave detecting unit and a dicroticnotch pressure DNP thereof linearly to a time axis between a time point T0 where the pulse wave detected by the pulse wave detecting unit rises and a time point T1 where a dicroticnotch thereof appears, whereby the pulse wave and the Korotkoff sound waveform are superposed on a graph with a time axis in common;

low pressure period superposing means for applying a pressure axis between the dicroticnotch pressure DNP of the Korotkoff sound waveform recorded by the sound wave detecting unit and a diastolic pressure DP thereof linearly to a time axis between the time point T1 where the dicroticnotch of the pulse wave detected by the pulse wave detecting unit appears and a time point T2 where the pulse wave reaches a diastolic pressure DP, whereby the pulse wave and the Korotkoff sound waveform are superposed on the graph; and blood circulatory trouble displaying means for giving a diagnostic envelope for diagnosis which connects points at predetermined peak positions of the respective Korotkoff sound waveforms on the graph, dividing the time axis of the graph in a plurality of sections, associating the respective sections with respective parts of the human body, and comparing the diagnostic envelope with predetermined reference envelopes in the respective section, and when any of the respective sections has an interval between the two which exceeds a predetermined limit, displaying a part of the human body associated with such a section as a blood circulation troubled part.

BRIEF DESCRIPTION OF THE DRAWINGS

FIG. 5b is a partially enlarged view of the graph of FIG. 5a;

FIG. 8b is a partially enlarged view of the graph of FIG. 8a;

FIG. 16b is a partially enlarged view of the graph of FIG. 16a;

FIG. 21 is a waveform view of an approximate aortic wave of a normal person detected by the apparatus of FIG. 13;

FIG. 22 is a wavform view of an approximate aortic wave of a patient detected by the apparatus of FIG. 13;

BEST MODE FOR CARRYING OUT THE INVENTION

§1 Pulse Wave Detecting Apparatus I 1.0 Basic Principle

The embodiment which will be disclosed in §1 is of the pulse wave detecting apparatus of the first to the third features of the present invention relate to. This invention is based on the finding of the basic principle that when a cuff is wound on an upper arm, and a pressure is applied to this cuff on required conditions, pulse waves equivalent to aortic waves can be obtained on the upper arm. When a sufficient pressure is applied to the cuff, the blood flow of the upper arm can be shut, and as the pressure is gradually reduced, pulse waves passing the cuff are detected. These pulse waves are, at the first, small, but become larger as the pressure on the cuff is reduced. The inventor of the present application has found that a pulse wave which passes the cuff to be detected when a pressure applied to the cuff agrees with a diastolic pressure DP is approximate to an aortic wave near the heart. In the pulse wave detecting apparatus according to this embodiment, Korotkoff sounds are monitored to judge a pressure of the cuff has reached a diastolic pressure DP when a Korotkoff sound reaches a set value. The pressure control means of this apparatus has a function of retaining a reference internal pressure of the cuff at a constant value when a Korotkoff sound has reached the set value. Accordingly the pulse waves outputted, during a time of the retention, by pulse wave outputting means are approximate to aortic waves near the heart. Thus, without directly measuring aortic waves near the heart, pulse waves approximate to the aortic waves can be measured on an upper arm.

1.1 Basic Constitution of the Apparatus

Figure 1:
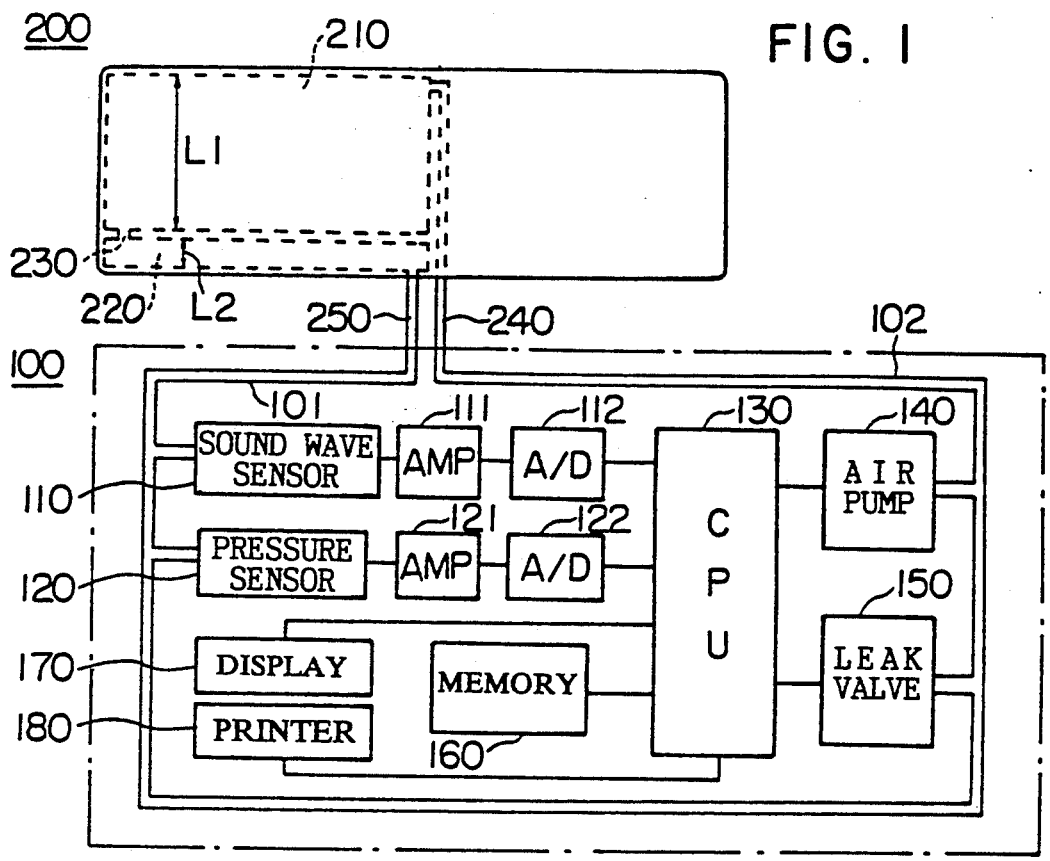
FIG. 1 is a block diagram of a structure of the pulse wave detecting apparatus according to a first embodiment of this invention.
Figure 2:
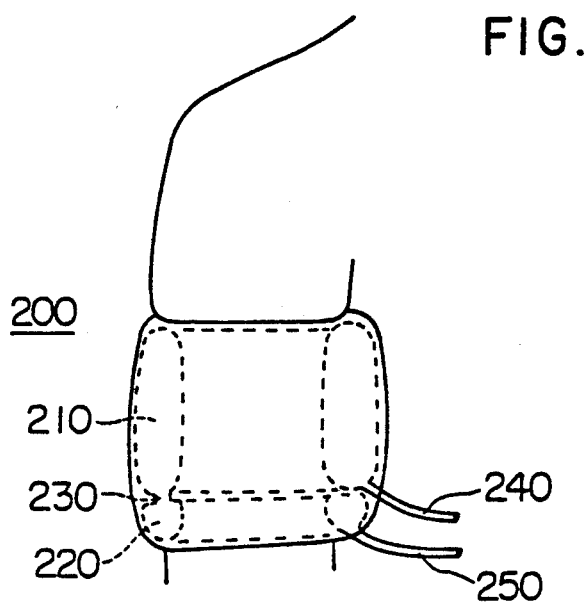
FIG. 2 is a view of a state of a cuff involved in the apparatus of FIG. 1 in which the cuff is put around an upper arm.

FIG. 1 is a block diagram of the pulse wave detecting apparatus according to an embodiment of this invention. This apparatus comprises an apparatus body 100 (enclosed by the one dot chain line), and a cuff 200. The cuff 200 has a blood flow shutting bag 210 for shutting the blood flow of an upper arm, and a detection bag 220 for detecting pulse waves which have passed the blood flow shutting bag 210. The blood flow shutting bag 210 has a size sufficient to shut the blood flow, and in this embodiment the length L1=about 12 cm in FIG. 1. The detection bag 220 is sufficiently smaller than the blood flow shutting bag 210, and in this embodiment the length L2=about 2 cm in FIG. 1. When the detection bag 220 is excessively large, its air volume is so large that pulse waves impinging against the air volume cannot be sufficiently detected. Both bags 210, 220 are interconnected with an intermediate communication passage 230. A conduit 240 for conveying air is extended outside from the blood flow shutting bag 210, and from the detection bag 220 is extended outside a conduit 250. This cuff 200 is put around on an upper arm for use as shown in FIG. 2.

The device body 100 has the following constitution. A sound wave sensor 110 and a pressure sensor 120 are connected to a piping 101 connected to the conduit 250. Both sensors are in principle those which detect a pressure in the detection bag 220 conveyed through the conduit 250. The pressure sensor 120 is designed to detect a pressure change of a frequency band of pulse waves, and the sound wave sensor 110 is designed to detect a frequency band of sound waves, especially a frequency band (30 to 80 Hz) of Korotkoff sounds. An analog signal detected by the sound wave sensor 110 is amplified by an amplifier 111, converted to a digital signal by an A/D converter 112 and supplied to a CPU 130. Similarly an analog signal detected by the pressure sensor 120 is amplified by an amplifier 121, converted to a digital signal by an A/D converter 122 and supplied to the CPU 130. A piping 102 connected to the conduit 240 is connected to an air pump 140 and a leak valve 150. The air pump 140 and the leak valve 150 are controlled by the CPU 130. The piping 101 and the piping 102 are interconnected. The blood flow shutting bag 210 and the detection bag 220 are also interconnected by the communication passage 230. Accordingly the blood flow shutting bag 210 and the detection bag 220 are kept under the same pressure. But, because the capacity of the blood flow shutting bag 210 is larger, small amplitude pressure changes appear in the detection bag 220. Consequently it is preferable to connect the sound wave sensor 110 and the pressure sensor 120 near the conduit 250. The CPU 130 is connected to a memory 160 for storing data, a display 170 for displaying the data, and a printer 180 for outputting the data.

1.2 Pulse Waveform

Figure 3:
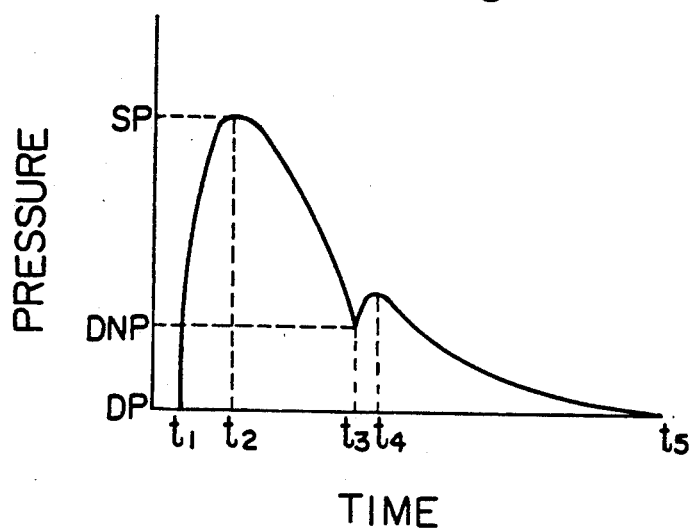
FIG. 3 is a waveform of the general aortic wave.
Figure 4:
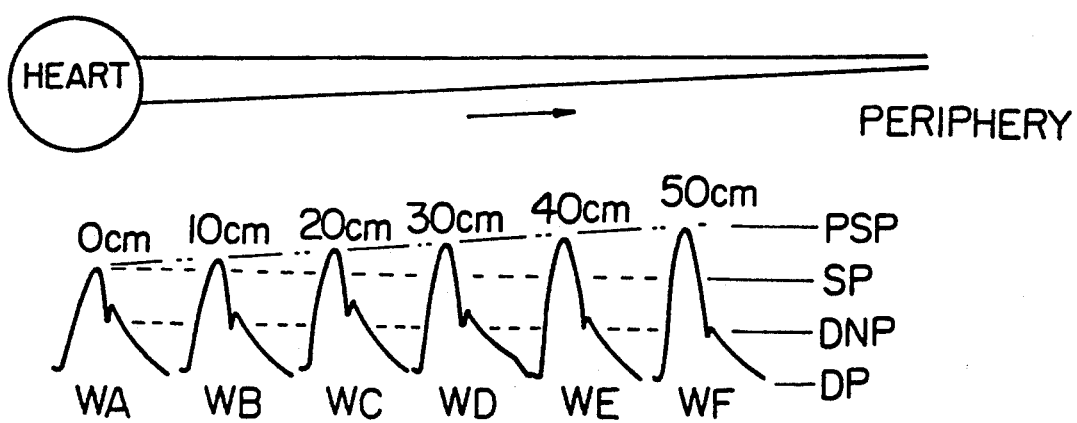
FIG. 4 is a view of changes of a pulse wave from the heart to the periphery.

Here it is simply explained what the aortic wave to be measured by this apparatus is. FIG. 3 shows the basic waveform of this aortic wave. As shown in FIG. 3, the aortic wave is indicated by time taken on the horizontal axis and the pressure taken on the vertical axis. The aortic wave has a waveform exhibiting a blood pressure change near the heart and shows a movement of the left ventriclary myocardium of the heart as it is. In FIG. 3 the heart is in a diastolic period until a time t1, and its pressure is a diastolic pressure DP. From the time t1 to t2 the heart contracts, and the pressure rises to a systolic pressure SP. Then the heart begins to expand and close the aortic valve at a time t3. Accordingly a small peak appears at a time t4. This peak is a dicroticnotch, and a pressure of a trough immediately before the peak is called dicroticnotch pressure DNP. The pressure gradually reduces from the time t4 to t5, and again the heart returns to the diastolic pressure DP. This pressure change occurs at each beat of the heart, the beat propagates as a pulse from the heart to all over the body through the arteries. But the pulse wave originated in the heart goes on changing its waveform as it propagates to the periphery. FIG. 4 shows changes of the waveform. The waveforms WA to WF are those of a pulse wave measured by blood vessel catheter measuring method at a part distant by 0 cm to 50 cm from a part directly above the aortic valve of the heart to the periphery. The waveform WA corresponds to the aortic wave near the heart in FIG. 3. It is seen that the high frequency component gradually increases as the pulse wave propagates to the periphery, and the peripheral systolic pressure PSP goes on increasing. This is because the blood vessels become thinner toward the periphery, and the resistance increases. Thus, because a pulse wave changes its waveform toward the periphery, a pulse wave (e.g., pulse wave WF) normally measured on an upper arm is considerably different from an aortic wave near the heart. According to this invention, a pulse wave equivalent to an aortic wave can be obtained on an upper arm.

1.3 Measuring Operation

Figure 5A:
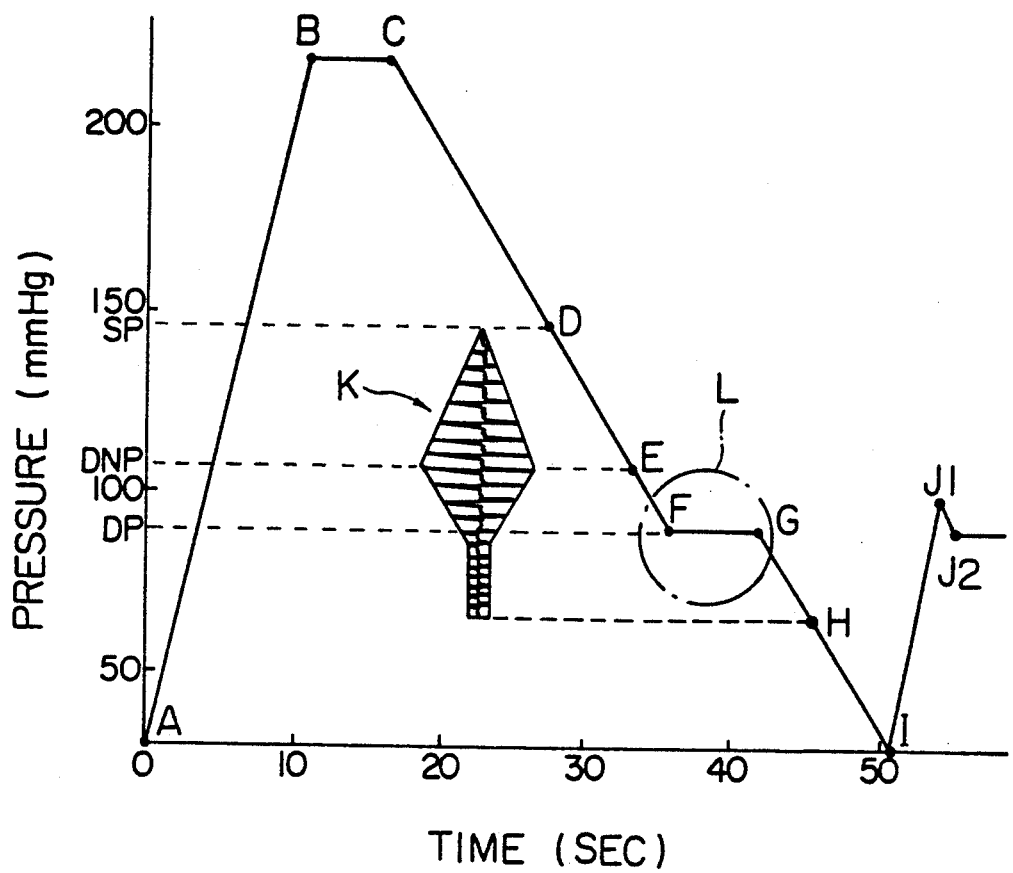
FIG. 5a is a graph explaining a measuring principle of the apparatus of FIG. 1.
Figure 5B:
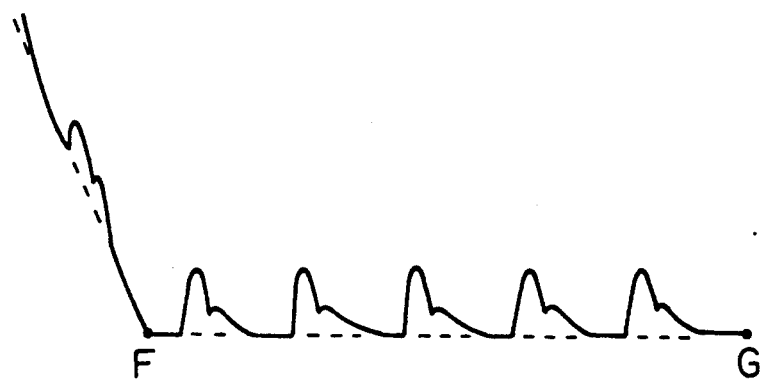

FIG. 5a is a graph explaining the measuring operation of this apparatus. FIG. 5b is a partially enlarged view. The pressure of the blood flow shutting bag 210 and of the detection bag 220 can be controlled by the air pump 140 and the leak valve 150. That is, when a pressure is increased, the air pump 140 is operated to feed air into the bags, and when the pressure is decreased, the leak valve 150 is opened to leak the air in the bag.

Figure 6A:
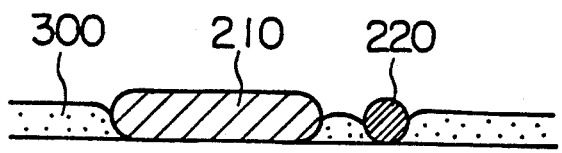
FIGS. 6a to 6e are sectional views explaining relationship between the cuff and a pulse wave clearing the same.

In a measuring operation, the cuff 200 is put around an upper arm of a person to be measured, and a measurement start switch (not shown) is turned on. FIG. 5a shows changes of the pressure in the bags following the start of the measuring operation. That is, when the measuring operation is started, the CPU 130 actuates the air pump 140 to feed air into the bags and gradually increase pressure in the bags (Point A to B in the graph). The blood flow shutting bag 210 increasingly presses the artery until its pressure completely shuts the blood flow (Point B). FIG. 6a is a sectional view explaining the relationship between the cuff 200 (blood flow shutting bag 210 and the detection bag 220), and the artery 300. The left side as viewed in FIGS. 6a to 6e is the heart, and the right side is the periphery. A pulse wave normally propagates from the left to the right, but because of the high pressure of the blood flow shutting bag 210, the pulse wave cannot clear the blood flow shutting bag 210. Here this pressure value is retained for a set period of time (Point B to C) to confirm the presence of air leakage of both bags 210, 220. If air leakage is found, the air is immediately discharged, and the measuring operation is stopped, alarming the occurrence of an abnormality. When no air leakage is found, the CPU 130 proceeds to open the leak valve 150 bit by bit to decrease the pressure (Point C to D). Then at Point D a Korotkoff sound is generated. The waveform K in the graph shows amplitudes of the Korotkoff sound obtained corresponding to pressure values gradually decreased from the pressure value at Point D. The occurrence of the Korotkoff sound when the pressure has passed Point D is due to that a part of the pulse wave begins to pass the blood flow shutting bag 210 against the pressure of the blood flow shutting bag 210.

Figure 6B:
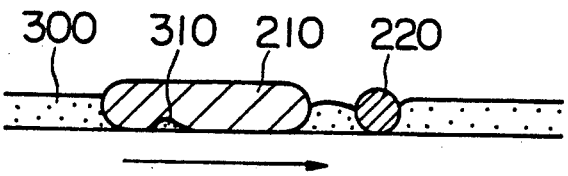
Figure 6C:
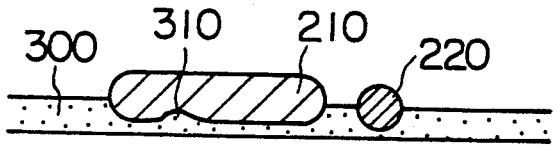
Figure 6D:
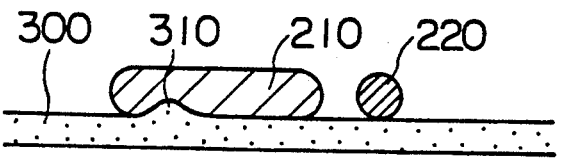
Figure 6E:
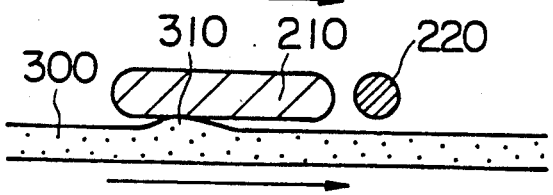

It is known that the pressure at Point D corresponds to a systolic pressure SP. As the pressure is further decreased from Point D, as shown in FIG. 6c, the pulse wave easily clears the blood flow shutting bag 210, and the Korotkoff sound becomes maximum at Point E in FIG. 5a. Hereafter the Korotkoff sound becomes smaller, and after Point F, the Korotkoff sound have constant amplitudes. It is known that a pressure at Point F corresponds to a diastolic pressure DP, and this correspond to the state of FIG. 6d. A characteristic of this device is that when a pressure is decreased down to Point F, the diastolic pressure DP is retained for some time (Point F to G) for the detection of the pulse wave. When the detection of the pulse wave is over, the pressure is further lowered (Point G to H). As shown in FIG. 6e, the cuff 200 floats on the artery 300. When the pressure is further lowered from Point H, the Korotkoff sound vanishes, and the pressure reaches Point I. When another measuring operation is repeated, the pressure is raised from Point I to Point J1, and then the pressure is lowered from Point J1 to Point J2 (diastolic pressure). This pressure is retained constant, and another measuring operation is started. Thus another measuring operation can be repeated without raising the pressure to Point B by storing a diastolic pressure DP at Point F, and raising the pressure to Point J1 (a little higher pressure than an diastolic pressure DP) and then lowering the pressure to the diastolic pressure DP.

1.4 Detection Pulse Wave

Here the method for detecting pulse waves will be explained. Pulse waves are pressure changes within the artery 300, and are measured in pressure values. As shown in FIGS. 6a to 6e, a pulse wave 310 which has cleared the blood flow shutting bag 210 impinges on the detection bag 220. Because the detection bag 220 has a smaller capacity than the blood flow shutting bag 210, the loss of a high frequency component of the pulse wave which has reached the detection bag 220 is little. Accordingly even pulse waves of small amplitudes can be detected. Small pressure changes of the detection bag 220 are detected by the pressure sensor 120. The blood flow shutting bag 210, whose capacity is large, does not have large pressure changes due to the high frequency component of the pulse wave. Here when a pressure value per se detected by the pressure sensor 120 is noted, it is found that two factors are multiplexed. One of the factors is a pressure of the blood flow shutting bag 210, and the other is a change of a pressure of the detection bag 220 due to a pulse wave. The former is here called reference internal pressure, and the other is called pulse wave pressure. Because the detection bag 220 is connected to the blood flow shutting bag 210 through the communication passage 230, when no pulse wave impinges on the detection bag 220, the pressure of the detection bag 220 is a reference internal pressure. The graph of FIG. 5a shows this reference internal pressure. The pressure detected by the pressure sensor 120 is actually this reference internal pressure multiplexed with a pulse wave pressure. FIG. 5b is an enlarged view of the portion L of FIG. 5a. In this enlarged view, pressure values multiplexing this reference internal pressure (indicated by the broken line in FIG. 5b) and a pulse wave pressure is indicated by the solid line. Between Point F and point G this reference internal pressure is maintained at a diastolic pressure DP, and a pulse wave rides on this diastolic pressure DP.

Figure 7:
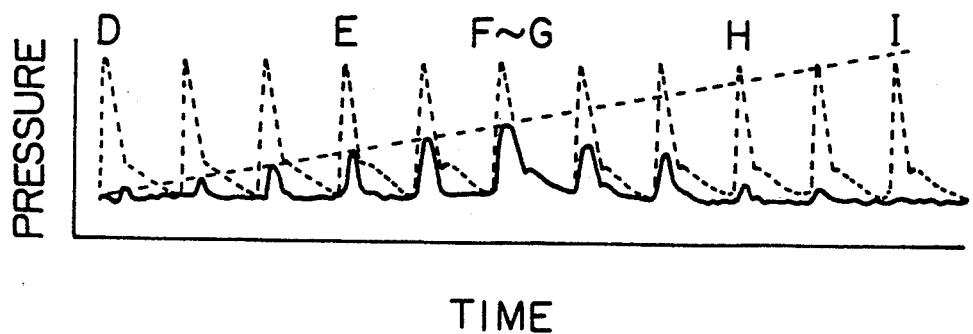
FIG. 7 is a view explaining the relationships between the cuff and detected pulse waves.

As shown in FIG. 4, a pulse wave on an upper arm (e.g., Pulse wave WF) is different from an aortic wave (Pulse wave WA). But the inventor has found that a pulse wave detected by the detection bag 220 when the blood flow shutting bag 210 is kept at a diastolic pressure DP is approximate to an aortic wave even though the pulse wave is detected on an upper arm. It is difficult to exactly analyze theoretically the mechanism for this finding, but the inventor thinks that the blood flow shutting bag 210 functions as a low pass filter, and high frequency component of a pulse wave is cut. That is, it is presumed that, as shown in FIG. 4, a pulse wave increases its high frequency component as the pulse wave propagates to the periphery due to increases of blood vessel resistance, but when a pulse wave (Pulse wave WF) at an upper arm clears the blood flow shutting bag 210, this high frequency component is cut, whereby a wave approximate to its original aortic wave (Pulse wave WA) is extracted. Accordingly it is necessary that the width (L1 in FIG. 1) of the blood flow shutting bag 210 is sufficient to function as a low pass filter. It has been confirmed experimentally that the blood flow shutting bag 210 is usually able to do this function when its width is 9 cm or larger. Thus a wave approximate to an aortic wave can be obtained when a pressure of the blood flow shutting bag 210 is equal to a diastolic pressure DP. Therefore, as shown in FIG. 5a, when a pulse wave is detected between Point F and Point G where a reference internal pressure is maintained to a diastolic pressure DP, the detected pulse wave can be used as the aortic wave. In the succeeding measuring operations, pulse waves detected at Point J2 and the following points can be used as the aortic wave. Here it is explained for reference what pulse waves can be obtained when the blood flow shutting bag 210 is not at a diastolic pressure DP (i.e., ranges other than that range between Points F and G). FIG. 7 shows pulse waves detected between Points D and I. In FIG. 7 the pulse waves depicted by the solid line are those detected by the pressure sensor 120 of this device, and the pulse waves depicted by the broken line are those (Pulse wave WF in FIG. 4) detected on an upper arm. The reference marks above the pulse waves indicates that the pulse waves are detected at the points indicated by the reference marks in FIG. 5a. The pulse waves with no reference marks are those detected at the intermediate points between the points with the reference marks. As shown, when a pressure is reduced gradually from Point D, the amplitude of the detected pulse waves gradually increases. The amplitude of the pulse wave becomes maximum at Point F (to Point G), and thereafter the amplitude goes on decreasing. By comparing the pulse wave depicted by the solid line at Point F with that depicted by the solid line there, it is seen that the high frequency component is cut. It has to be noted that the amplitude of the pulse wave does not always proportion with that of its Korotkoff sound. The Korotkoff sound peaks at Point E as shown in FIG. 5a, but as shown in FIG. 7, the pulse wave does not peak at Point E. It is considered that the relationship between the cuff 200 and the artery 300 is as shown in FIG. 6d at Points F to G. That is, at Points F to G, a reference internal pressure of the cuff 200 and a diastolic pressure DP of the artery are competing, and a pulse wave can clear the blood flow shutting bag 210 and also can give a sufficient impact to the detection bag 220. When the reference internal pressure is higher than this, as shown in FIGS. 6a to 6c, a pulse wave cannot fully clear the blood flow shutting bag 210 and cannot give a sufficient impact to the detection bag 220. When the pressure of the cuff 200 is lower than this, as shown in FIG. 6e, the detecton bag 220 leaves the artery 300, and even though a pulse wave fully clears the blood flow shutting bag 210, a sufficient impact cannot be given to the detection bag 220.

1.5 Operation of the Apparatus Body

A pulse wave thus detected by the pressure sensor 120 between Points F and G is supplied as a digital signal to the CPU 130. In this apparatus, the pulse data supplied to the CPU 130 is first stored by the memory 160. A plurality of pulse waves are detected continuously between Points F and G as shown in FIG. 5b, and these pulse wave data are outputted respectively and in a waveform of their average pulse wave by the printer 180. A systolic pressure SP value at Point D, a dicrotic-notch pressure DNP value at Point E, a diastolic pressure DP value at Point F, and a pulse rate are displayed on the display device 170.

Figure 8A:
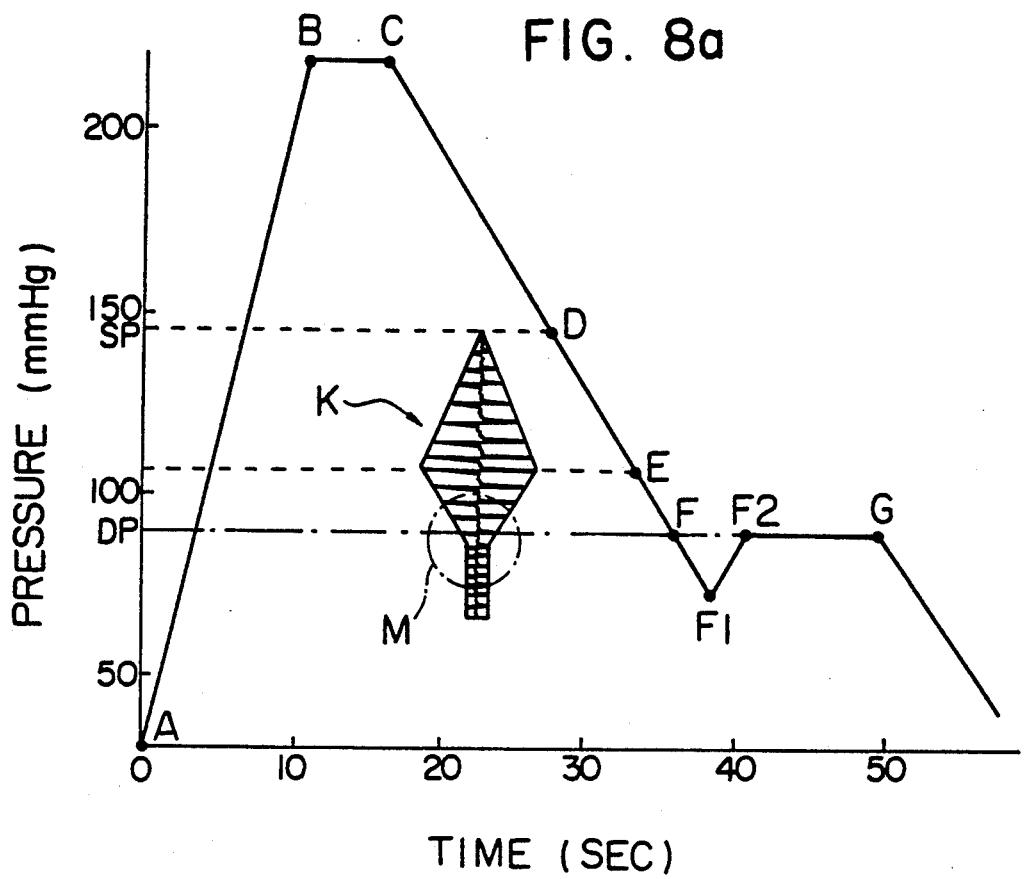
FIG. 8a is a graph explaining an actual measuring operation of the apparatus of FIG. 1.
Figure 8B:
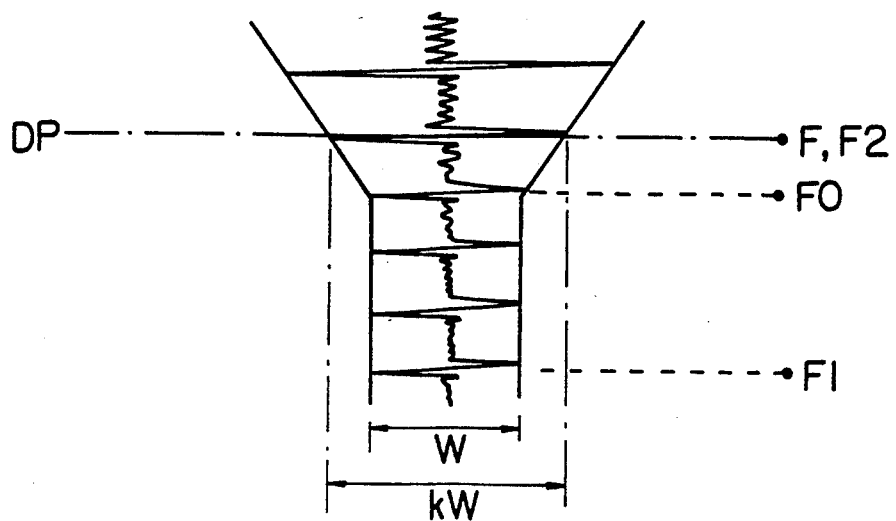

The CPU 130 mantains a pressure constant when the pressure reaches Point F. Actually, however, it is difficult to correctly judge the pressure has reached Point F. The judgement that the pressure has reached Point F is made based on the detection that the Korotkoff sound has become smaller, and the amplitude does not change any more. But because the pressure is decreased at a certain rate, it tends to happen that the actual pressure has already passed Point F and is lower when the CPU 130 recognizes the arrival of the pressure at Point F. Then in this invention is conducted the pulse wave detection as in FIG. 8a, which is based on the principle that the pulse wave detection is conducted based on the pressure control as in FIG. 5a. That is, a pressure continues to be decreased on the above described principle from Point D to Point F, and even past Point F, the pressure continues to be lowered. The amplitude of the Korotkoff sound is continuously monitored and when the amplitude of the Korotkoff sound does not change any more even with a pressure reduction for a set period of time, the pressure reduction is stopped (Point F1), and oppositely the pressure is gradually increased. An amplitude W of the Korotkoff sound at Point F1 is stored, and the amplitude of the Korotkoff sound is increased to kW (k: a set coefficient, e.g., k=1.5), the pressure is maintained constant there (Point F2). FIG. 8b is an enlarged view of the portion M of FIG. 8a and shows this more elaborately. As seen in this enlarged view of FIG. 8b, more exactly the point F where a diastolic pressure DP is not Point F0 where the amplitude of the Korotkoff sound becomes, for the first time, a constant value W, but a point before Point F0 by one beat. It was confirmed that, when the amplitude of the Korotkoff sound at Point F is represented by kW, k=around 1.5. Accordingly, when the pressure is lowered down to F1 as described above, the pressure is oppositely increased gradually, and when the amplitude of the Korotkoff sound becomes 1.5 times, Point F2 is taken as a point where the pressure is equal to a diastolic pressure DP. This coefficient k varies with patients but causes no problems in terms of the detection accuracy of an approximate aortic wave.

1.6 Detection Result of Approximate Aortic Wave

Figure 9:
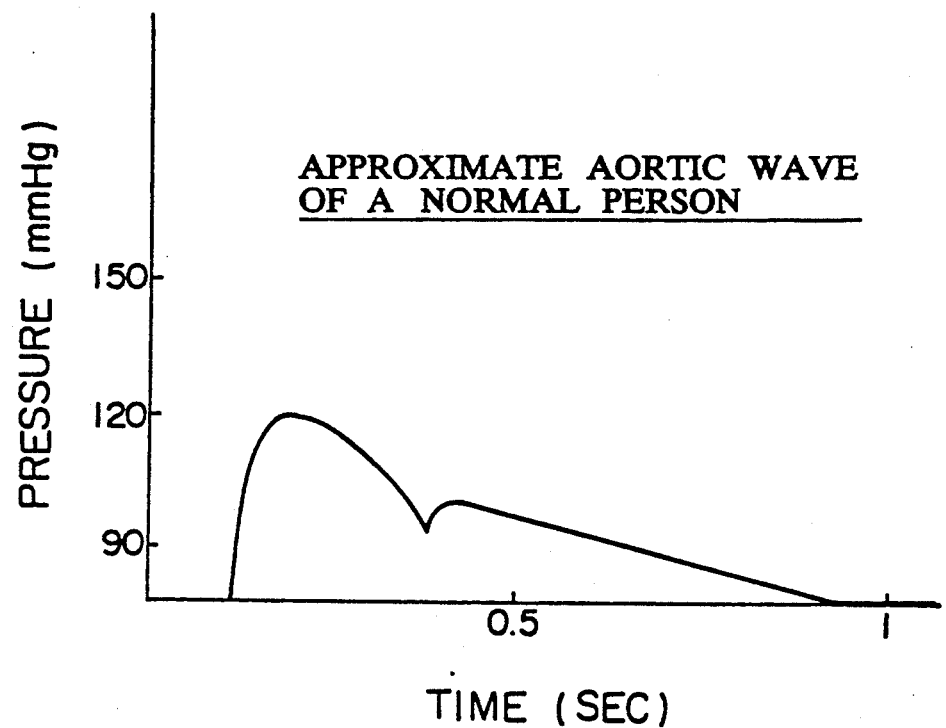
FIG. 9 is a waveform view of an approximate aortic wave of a normal person measured by the apparatus of FIG. 1.
Figure 10:
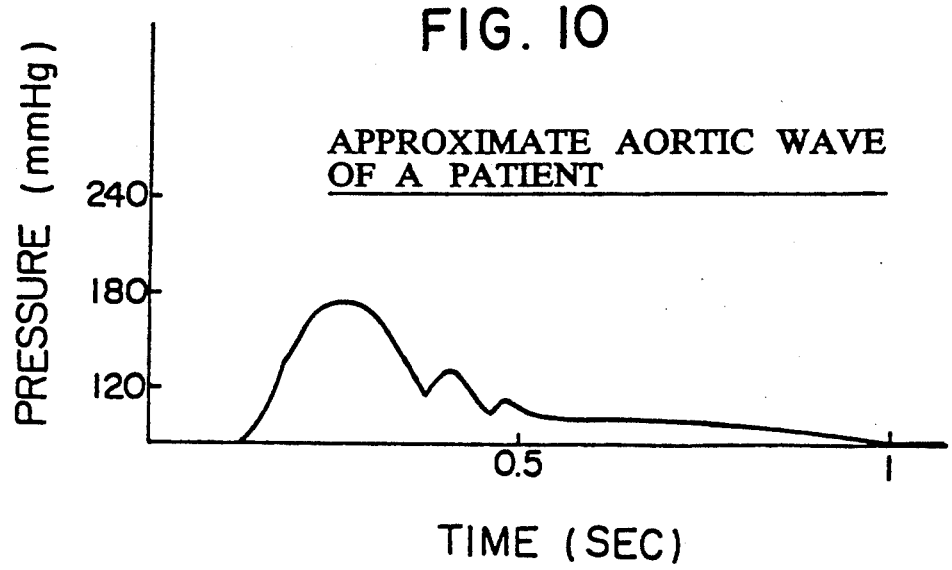
FIG. 10 is a waveform view of an approximate aortic wave of a patient detected by the apparatus of FIG. 1.

Finally, approximate aortic waves detected by this apparatus are shown in FIGS. 9 and 10. FIG. 9 shows a normal person's approximate aortic wave, and FIG. 10 shows an approximate aortic wave of a patient with a heart disease. These thus obtained aortic waves are approximate to those invasively measured by the conventional blood vessel catheter method. In addition, a characteristic of this device is that actual measured values of blood pressures are taken on the vertical axes, and actual times are taken on the horizontal axes, and not only the waveforms of a pulse wave, but also the blood pressure values can be obtained. It is very useful to the synthetic diagnosis of heart diseases to know thus non invasively blood pressure values as well as waveforms.

1.7 Modifications

Thus, this invention has been explained by means of one embodiment thereof but is not limited to the embodiment. In short, this invention is based on the finding that when a pressure is applied to a cuff put around an upper arm, a pulse wave approximate to an aortic wave is obtained at the upper arm. As long as pulse waves can be detected based on this principle, apparatuses of any structures can be used. In the above described embodiment, for example, it is recognized by Korotkoff sounds that a cuff pressure has become equal to a diastolic pressure DP, but it can be recognized by other methods (one example will be explained in §2). In cases that it is recognized by Korotkoff sounds, methods other than the above described method used in the embodiment are considered. For example, a microphone is disposed near the detection bag to detect Korotkoff sounds by the microphone.

Figure 11:
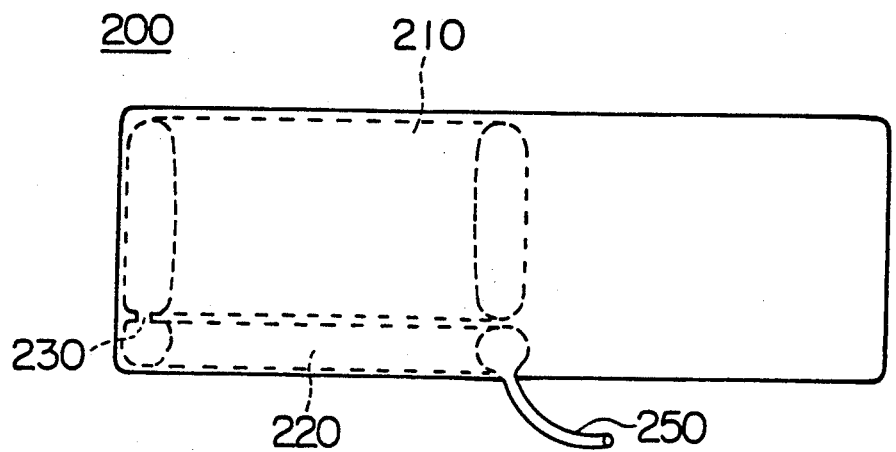
FIG. 11 is a view of another cuff used in the apparatus of FIG. 1.
Figure 12:
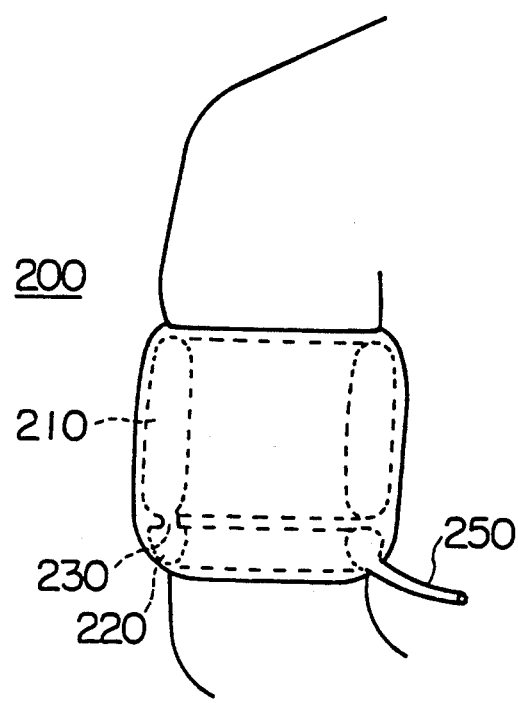
FIG. 12 is a view of a state of the cuff of FIG. 11 in which the cuff is put around an upper arm.

The cuff is not limited to that used in the above described embodiment. Different cuffs may be used. FIG. 11 shows one example of the different cuffs. As seen in comparison of the cuff of FIG. 11 with that of FIG. 1, Only the conduit 250 is led outside, and no conduit is led out from the blood flow shutting bag 210. FIG. 12 shows the state of this cuff put on an upper arm. Because the blood flow shutting bag 210 is connected to the detection bag 220 through the communication passage 230, even with the conduit 250 alone, the pulse wave detection involved in this invention can be achieved. It is rather preferable to use such cuff with one conduit because of the following merits.

(1) In the case two conduits are provided, the erroneous connection of the conduits to the device body 100 (the two conduits are connected erroneously to the other position). But such error cannot happen with cases one conduit is provided.

(2) Because the communication passage is only one inlet and outlet to and from the blood flow shutting bag 210, gains of detection of pressure changes can be improved.

(3) The provision of one conduit results in smaller weights and lower consts.

As described above, according to this invention, a cuff is put around an upper arm, whereby pulse waves approximate to an aortic waves can be detected. Consequently the non invasive measurement of waveforms of aortic waves concurrent with the measurement of blood pressure values can be facilitated.

§2 Pulse Wave Detection Apparatus II 2.0 Basic Principle

The embodiment disclosed in §2 is a pulse wave detecting apparatus relating to the fourth to the sixth features of the present invention. The basic principle of this apparatus is the same as that of the apparatus disclosed in §1. That is, this apparatus is based on the finding of the inventor of the present application that a pulse wave which clears a cuff when a cuff pressure agrees with a diastolic pressure DP is approximate to an aortic wave near the heart. In the apparatus disclosed in §1, it is judged by monitoring Korotkoff sounds that a cuff pressure has reached a diastolic pressure DP. But in the pulse wave detecting apparatus disclosed in §2, a pulse wave coming into a cuff at the forward end thereof, and a pulse wave going out of the cuff at the rear end of thereof are monitored, and when the lower parts of both pulse waves agree with each other, it is judged that a cuff pressure has reached a diastolic pressure DP. The pressure control means of this apparatus has the function that when both pulse waves agree with each other with a required precision, the reference internal pressure of the cuff is retained at a constant value. Accordingly pulse waves outputted by the pulse wave outputting means while the reference internal pressure is maintained at a constant value are approximate to aortic waves near the heart. Thus pulse waves approximate to aortic waves can be measured on an upper arm without directly measuring pulse waves near the heart.

2.1 Basic Structure of the Apparatus

Figure 13:
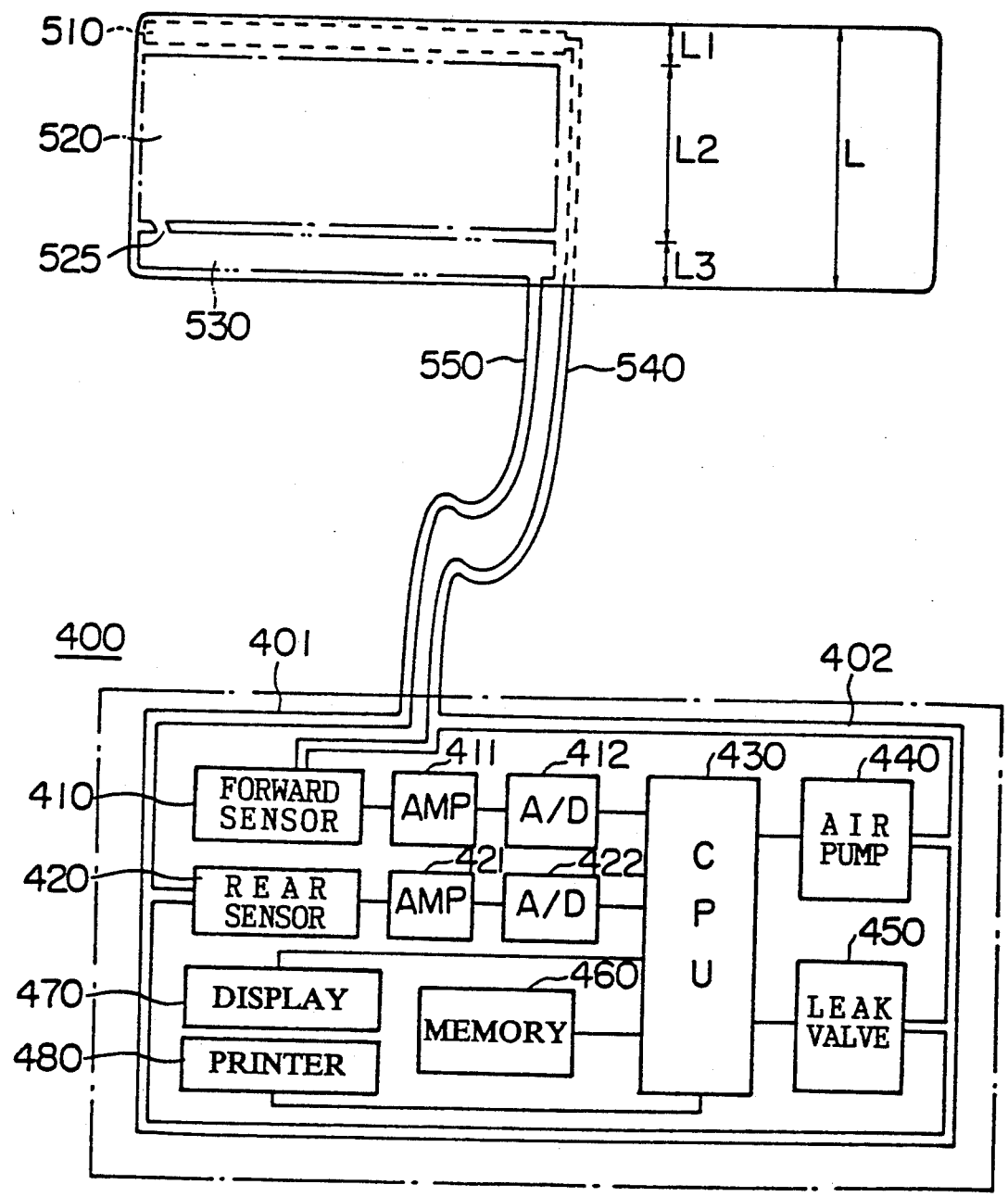
FIG. 13 is a block diagram of a structure of the pulse wave detecting apparatus according to a second embodiment of this invention.

FIG. 13 is a block diagram of the basic structure of the pulse wave detecting apparatus according to one embodiment of this invention. This apparatus is largely divided in two constituent sections of an apparatus body 400 (enclosed with the one dot chain line), and a cuff 500. The cuff 500 comprises a blood flow shutting bag 520 (indicated by the one dot line) for shutting the blood flow of an upper arm, a forward detection bag 510 (indicated by the broken line), and a rear detection bag 530 (indicated by the two dot line) for detecting a pulse wave passing the blood flow shutting bag 520. The blood flow shutting bag 520 has a length sufficient to shut the blood flow, and in this embodiment the length of the bag 520 indicated by L2 in the drawing is L2=about 10 cm with respect to the total length of the cuff L=14 cm. The forward and the rear detection bags 510, 530 are made smaller compared with the blood flow shutting bag 520, and in this embodiment the length of the forward detection bag 510 indicated by L1 in the drawing is L1=1.5 cm, and that of the rear detection bag 530 indicated by L3 in the drawing is L3=about 2.0 cm. If the bags 510, 530 are too big, a pulse wave impinging on them cannot be detected adequately because of their large air volumes. The blood flow shutting bag 520 and the rear detection bag 530 are in communication with each other through a communication passage 525 provided between them. A conduit 540 is extended from the forward detection bag 510 for letting the air out of the same. A conduit 550 is extended outside from the rear detection bag 530. This cuff 500 is put around an upper arm in the state shown in FIG. 14. When the cuff is put on in this state and air is fed to the respective bags to pressurize them, the artery 300 is pressed by the respective bags as shown in FIG. 15 (for the convenience of the illustration, the respective bags are spaced from each other, but actually the spacing is very small). When the pressure is increased, the artery 300 is pressed by the blood flow shutting bag 520. In this case, a pulse wave propagated from the left as viewed in the drawing, the pulse wave first impinges on the forward detection bag 510, and its high frequency component clears the forward detection bag 510 to impinge on the blood flow shutting bag 520. But because the blood flow shutting bag 520 has a large volume, the high frequency component of this incoming pulse wave is blocked by the blood flow shutting bag 520 and cannot reach the rear detection bag 530. When the pressure is decreased to pass the pulse wave, the pulse wave, which has cleared the blood flow shutting bag 520, impinges on the rear detection bag 530. Consequently the forward detection bag 510 incessantly detects a pulse wave, but the rear detection bag 530 detects the pulse wave only when the pulse wave has cleared the blood flow shutting bag 520.

The apparatus body 400 has the following structure. A forward sensor 410 is provided in a piping 402 connected to the conduit 540, and a rear sensor 420 is provided in the piping 401 connected to the conduit 550. The forward sensor 410 measures a pressure of the forward detection bag 510, and the rear sensor 420 measures a pressure of the rear detection bag 530. Both sensors are designed so as to adequately measure frequency bands of pulse waves. An analog signal detected by the forward sensor 410 is amplified by an amplifier 411 and converted to a digital signal by an A/D converter 412 to be supplied to a CPU 430. Similarly an analog signal detected by the rear sensor 420 is amplified by an amplifier 421 and converted to a digital signal by an A/D converter 422 to be supplied to the CPU 430. An air pump 440 and a leak valve 450 are connected to the piping 402 connected to the conduit 540. The air pump 440 and the leak valve 450 are controlled by the CPU 430. The piping 401 and the piping 402 are connected to each other. The blood flow shutting bag 520 and the rear detection bag 530 are communicated with the communication passage 525. Resultantly the blood flow shutting bag 520 and the respective detection bags 510 and 530 are naturally kept under the same pressure. But because of a large volume of the blood flow shutting bag 520, high frequency pressure changes appear only in the forward detection bag 510 and the rear detection bag 530. Accordingly it is preferable that the forward and the rear sensors 410, 420 are connected respectively to the pipings 402, 401 near their associated conduit 540, 550. To the CPU 430 there are connected a memory 460 for storing data, a display 470 for displaying data, and a printer 480 for outputting data.

2.2 Measuring Operation

Figure 16A:
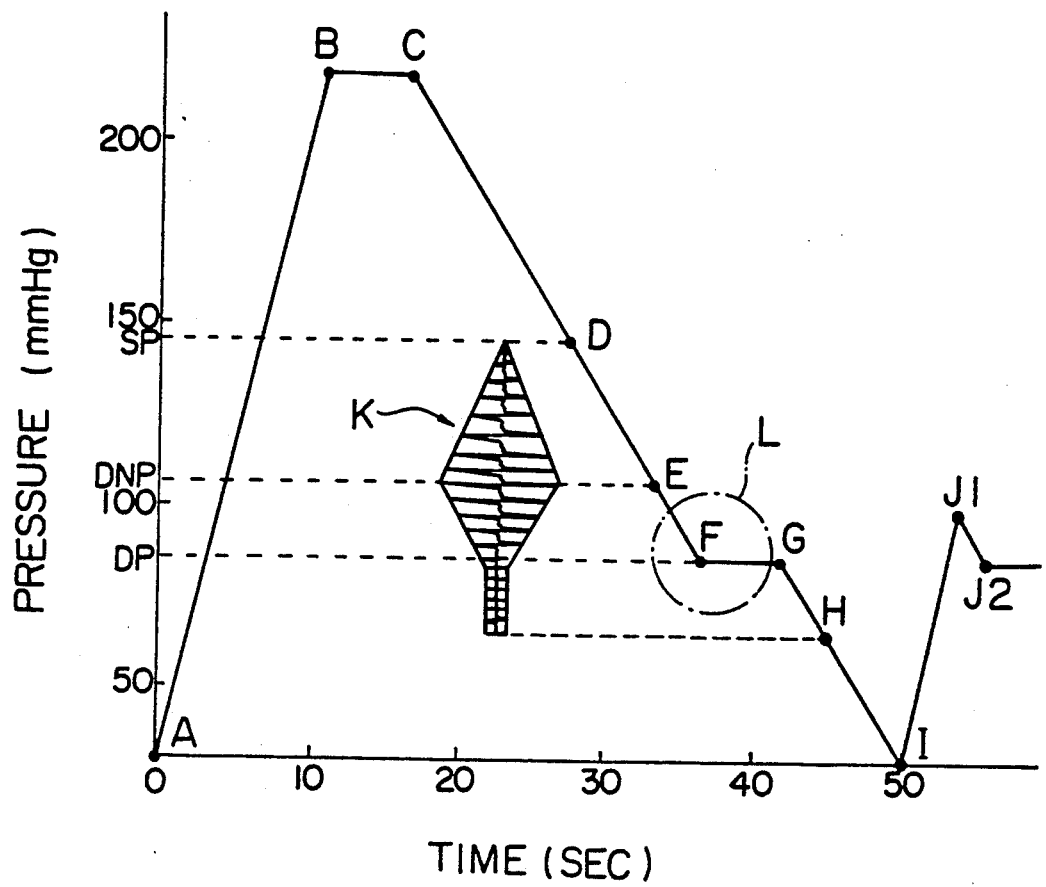
FIG. 16a is a graph explaining a measuring principle of the apparatus of FIG. 13.
Figure 16B:
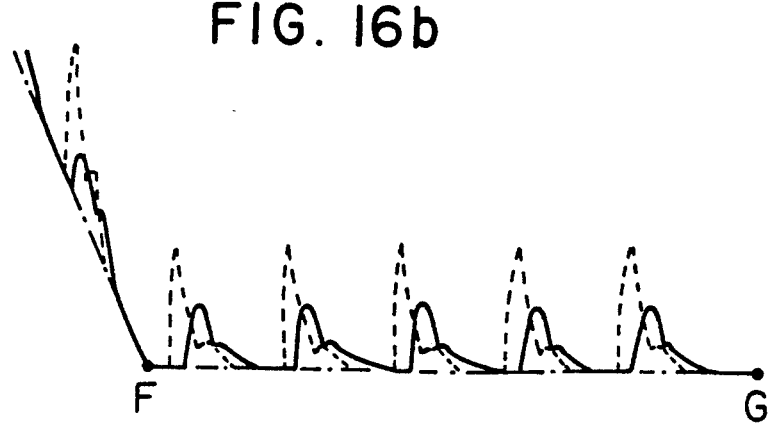

FIG. 16a is a graph explaining the measuring operation of this apparatus. FIG. 16b is a partial enlarged view of the graph. As described above, this apparatus includes the air pump 440 and the leak valve 450, so that the pressures of the blood flow shutting bag 520 and the respective detection bags 510, 530 can be controlled. That is, when the pressure is increased, the air pump 440 is operated to feed air into the bags, and when their pressures are decreased, the leak valve 450 is opened to leak out the air in the bags.

Figure 14:
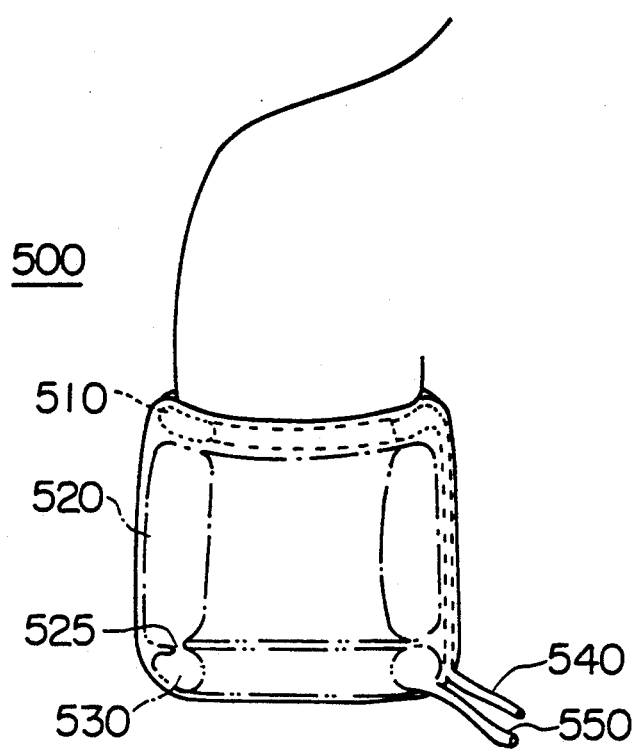
FIG. 14 is a view of a state of the cuff of FIG. 13 in which the cuff is put around an upper arm.
Figure 15:
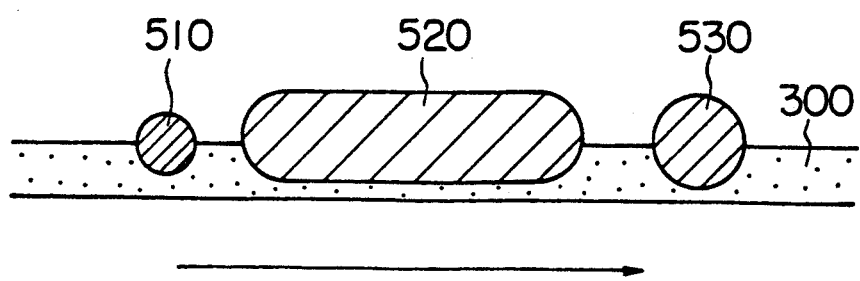
FIG. 15 is a sectional view of an artery pressed by the cuff of FIG. 14.
Figure 17A:
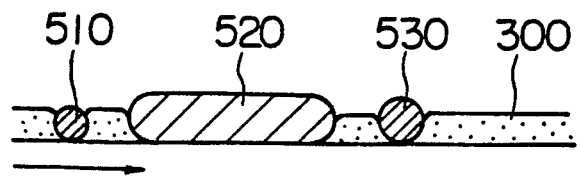
FIGS. 17a to 17e are sectional views explaining relationships betweent the cuff and a pulse wave clearing the cuff.
Figure 17B:
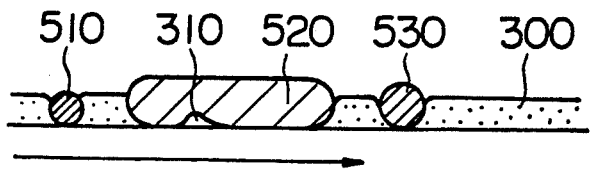
Figure 17C:
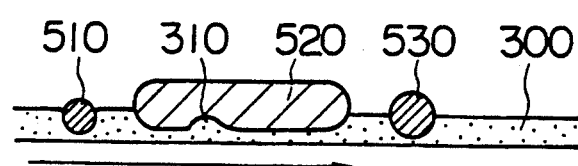
Figure 17D:
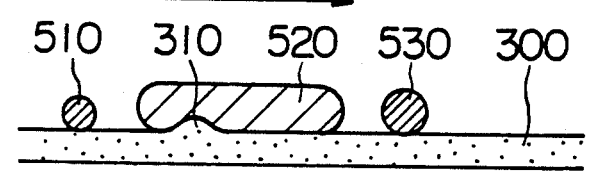
Figure 17E:
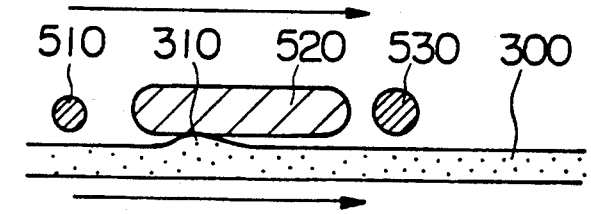

In a measuring operation, the cuff 500 is put around an upper arm of a person to be measured as shown in FIG. 14, and a measurement start switch (not shown) is pushed. The graph of FIG. 16a shows changes of pressures in the bags immediately after the start of a measuring operation. The operation of this device is the same as the device disclosed in §1 shown in FIG. 5a. That is, when a measuring operation is started, the CPU 430 actuates the air pump 440 to feed air into the bags to gradually increase their pressures (Point A to B in the graph). The blood flow shutting bag 520 gradually presses the artery and soon has a pressure which completely shuts the blood flow of the artery (Point B). FIG. 17a are sectional views showing the relationships of the cuff 500 (the blood flow shutting bag 520 and both detection bags 510, 530) with the artery 300. The heart is on the left side as viewed in FIG. 17a, and the periphery is on the right side. Pulse waves are propagated from the left to the right. As described above, the high frequency component of a pulse wave can clear the forward detection bag 510, but any components of the pulse wave cannot clear the blood flow shutting bag 520 because of its higher pressure. Accordingly, at this time, the forward sensor 410 detects the pulse wave on its way to the blood flow shutting bag 520, but the rear sensor 420 can detect none of the pulse wave. This pressure value is maintained for some time (Points B to C) to confirm the presence of leakage of the air of the bags. Subsequently the CPU 430 gradually opens the leak valve 450 to slowly lower the pressures (Point C to D). Then, at Point D Korotkoff sounds are generated. The waveform K in the graph indicates the amplitudes of the Korotkoff sounds obtained corresponding to the values of gradually decreased pressures from Point D. Thus Korotkoff sounds are generated after Point D. This is because a part of a pulse wave begins to clear the blood flow shutting bag 520 against the pressure thereof as shown in FIG. 17b. It is known that the pressure at Point D corresponds to the systolic pressure SP. As the pressure is further decreased from Point D, as shown in FIG. 17c, the pulse wave can more easily clear the blood flow shutting bag 520, and the Korotkoff sound becomes maximum at Point E. Then the Korotkoff sound gradually becomes smaller to be very small at Point F, and then a substantially constant amplitude continues. It is known that the pressure at Point F corresponds to the diastolic pressure DP, which corresponds to the state of FIG. 17d. This device is characterized as is the device disclosed in §1, in that the pressure is decreased to Point F, and the pressure DP at Point F is maintained for some time (Points F to G) in which the pulse wave is detected. When the detection of the pulse wave is over, the pressure is further decreased (Point G to I). At this time, the cuff 500 is afloat on the artery 300 as shown in FIG. 17e. In the case that the measuring operation is again performed, the pressure is increased form Point I to Point J1 and then is decreased from Point J1 to Point J2 (diastolic pressure DP). This pressure is maintained constant, and the pulse wave detection is again conducted.

2.3 Detection of Pulse Wave

Next, the pulse wave detection method will be explained. A pulse wave is a pressure change in the artery 300 and is measured as a pressure value. As shown in FIGS. 17b to 17e, the pulse wave 310 which has cleared the blood flow shutting bag 520 impinges on the rear detection bag 530. The rear detection bag 530 can detect even such a small amplitude pulse wave because of its smaller capacity than the blood flow shutting bag 520. This small pressure change is detected by the rear sensor 420. The blood flow shutting bag 520 is not much influenced, because of its larger capacity, by a pressure change due to a high frequency component. As described above, the forward sensor 410 is always detecting pressure changes. Here when a pressure value detected by a sensor 410 or 420 is noted, it is seen that the pressure value has two multiplexed factors. That is, one of the two factors is a pressure of the blood flow shutting bag 520, and the other is a pressure change due to a pulse wave impinging on the forward detection bag 510 or the rear detection bag 530. As in §1, here the former is called reference internal pressure, and the latter is called rear pulse wave pressure. Since all the bags are distantly communicated with the conduits as described above, the forward and the rear detection bags 510, 530 have a reference internal pressure when no pulse wave impinges thereon. FIG. 16a shows this reference internal pressure. A pressure detected by the forward detection bag 510 or by the rear detection bag 530 is actually a multiplexed pressure of this reference internal pressure. FIG. 16b is an enlarged view of the portion L in FIG. 16a. In this enlarged view, values of the multiplexed pressures of the reference internal pressure (indicated by the one dot chain line in FIG. 16b) and forward pulse wave pressures are graphed in the broken line, and values of the multiplexed pressures of the reference internal pressure and rear pulse wave pressures are graphed in the solid lines. In the graph of FIG. 16b, between Points F and G, as described above, the reference internal pressure is maintained at a diastolic pressure DP, and on the diastolic pressure DP are mounted forward pulse wave pressures and rear pulse wave pressures.

2.4 Operation of the Device Itself

Rear pulse waves thus detected by the rear sensor 420 between Points F and G are supplied as digital signals to the CPU 430. In this apparatus, the pulse wave data supplied to the CPU 430 are first stored in the memory 460. A rear pulse wave is continuously detected a plurality times between Points F and G as shown in FIG. 16b. These respective rear pulse wave data, and the waveform of their average pulse wave are outputted by the printer 480. A systolic pressure value SP at Point D, a dicroticnotch pressure value DNP at Point E, a diastolic pressure value DP at Point F, and a pulse rate are displayed by the display device 470.

The CPU 430 maintains the pressure at a constant value when a pressure reaches Point F. Then how is it judged whether or not a pressure has reached Point F, i.e., whether or not a pressure value has deceased to the diastolic pressure DP? The device disclosed in §1 judges the arrival of a pressure to Point F, based on Korotkoff sounds. But in this apparatus makes this judgement by a quite different, unique method.

Figure 18:
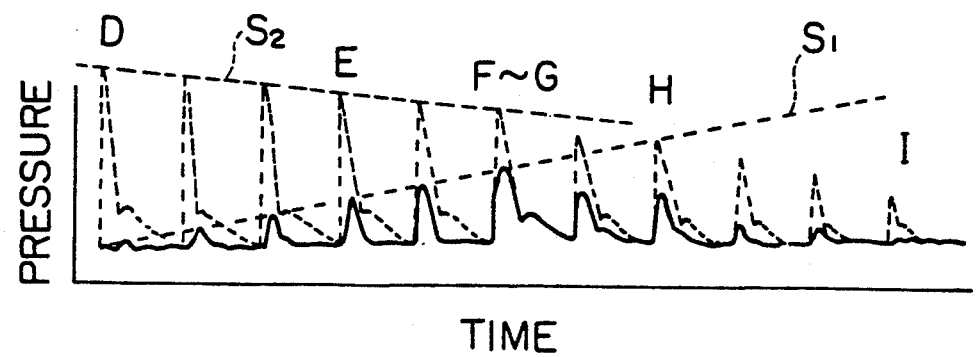
FIG. 18 is a waveform view explaining relationships between the cuff and a detected pulse wave.

To explain this jugement method, it is described what forward pulse waves and rear pulse waves are obtained when the blood flow shutting bag 520 has pressures other than the diastolic pressure (i.e., outside Points F to G). FIG. 18 is a view of various pulse waves detected between Points D and I in FIG. 16a. In FIG. 18 the waveform depicted by the solid line is of the rear pulse wave detected by the rear sensor 420, and the waveform depicted by the broken line is of the forward pulse wave (corresponding to the pulse wave WF in FIG. 4) detected by the forward sensor 410. The reference characters above pulse waves indicate that they are pulse waves detected under the reference internal pressures indicated by the reference characters in FIG. 16a. The wave pulses with no reference characters are those detected intermediate between the pulse waves with the reference characters. When the rear pulse wave depicted by the solid line is noted, as a pressure is gradually reduced from Point D, the amplitude of the detected rear pulse wave gradually increases. When the pressure reaches Point F (to Point G), the amplitude of the pulse wave becomes maximum and decreases thereafter. On the other hand, when the forward pulse wave depitcted by the borken line is noted, as the pressure is gradually decreased from Point D, the amplitude of the detected forward pulse wave as well decreases. This is because the shut blood flow is released (FIG. 17b), and a number of pulse waves 310 clearing the blood flow shutting bag 520 to the periphery gradually increases. When the pressure passes Point G, the amplitude of the pulse wave further reduces. This is because the forward detection bag 510 becomes afloat on the artery 300 as shown in FIG. 17e. Here the solid line pulse wave at Point F is compared with the broken line pulse wave there. Then it is found that when a high frequency component of the forward pulse wave (broken line) is cut off, it corresponds to the solid line rear pulse wave. It is supposed that the relationship between the cuff 500 and the artery 300 at Point F is as in FIG. 17d. That is, the reference internal pressure of the cuff 500 balances with the diastolic pressure of the artery 300. Pulse wave which has cleared the blood flow shutting bag 520 is filtered to give an impact to the rear detection bag 530 as an approximate aortic wave. If the cuff has a higher pressure than the reference internal pressure, as shown in FIGS. 17a to 17c, a pulse wave cannot fully clear the blood flow shutting bag 520, and a sufficient impact cannot be given to the rear detection bag 530. If the cuff 500 has a lower pressure than the reference internal pressure, as shown in FIG. 17e, the rear detection bag 530 leaves the artery 300, and even if a pulse wave has fully passed the blood flow shutting bag 520, the rear detection bag 530 is too apart from the artery 300, a sufficient impact cannot be given to the rear detection bag 530.

Now FIG. 18 is again noted. FIG. 18 suggests a significant method for judging whether or not the reference internal pressure has reached Point F, i.e., whether or not its pressure value has decreased to the diastolic pressure DP. That is, the forward wave pulse (broken line) and the rear wave pulse (solid line) at Point F perfectly agree with each other at the bottom part. Conversely, when their bottoms agree with each other, at this time the reference internal pressure of the cuff 500 is the diastolic pressure DP. Accordingly the CPU 430 gradually decreases the reference internal pressure from Point C in FIG. 16a, and each time a forward pulse wave supplied by the forward sensor 410 is compared with a rear pulse wave supplied by the rear sensor 420. When the CPU finds their bottoms agree with each other, the CPU 430 judges that the reference internal pressure has arrived at Point F, maintains the reference internal pressure constant until Point G by controlling the pressure. This device detects the forward pulse wave in the sake of this comparison.

Figure 19:
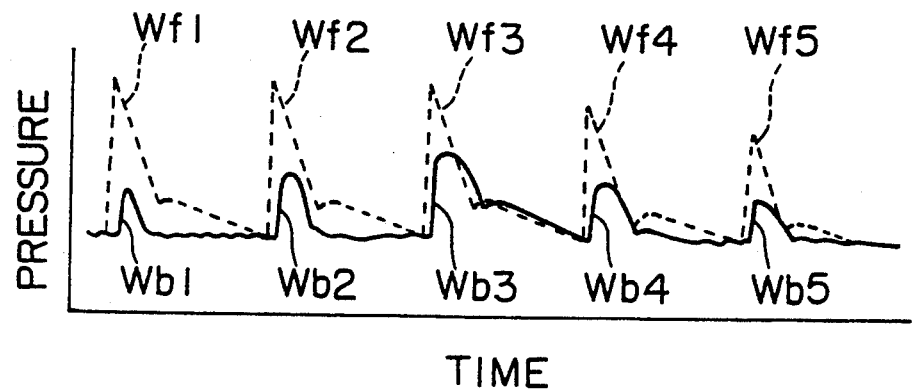
FIG. 19 is a view explaining relationships between a forward and a rear pulse waves detected by the apparatus of FIG. 13.
Figure 20:
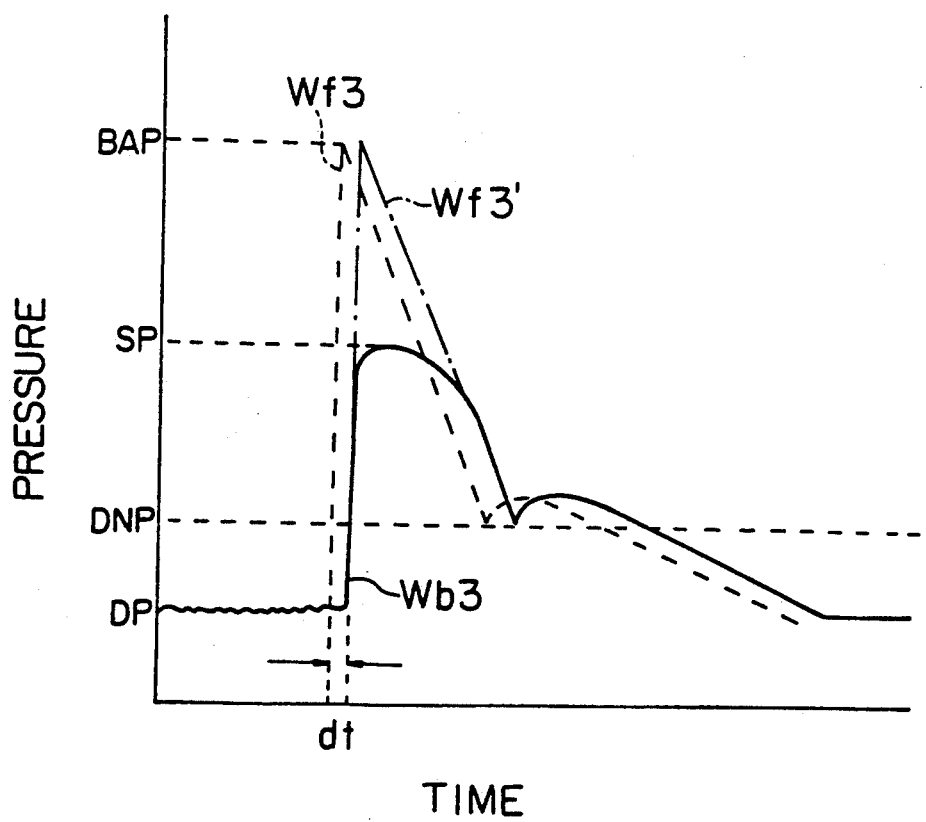
FIG. 20 is a partially enlarged view of FIG. 19.

Actually to conduct the above described pressure control, both pulse waves must be compared, taking into consideration a delay time of the rear pulse wave. That is, a forward pulse wave and the rear pulse wave do not simultaneously enter the CPU 430. This is because a pulse wave takes a delay time dt, as shown in FIG. 19, to clear the blood flow shutting bag 520 to be detected at the rear detection bag 530 after detected at the forward detection bag 510. Accordingly, when forward pulse waves Wf1 to Wf5, and rear pulse waves Wb1 to Wb5 are compared respectively on the same time axis, there occurs a time delay dt between both pulse waves. Then the CPU 430 temporarily stores in the memory 460 the waveform data of a forward pulse wave and the rear pulse wave, and subsequently delay the forwad pulse wave so as to agree the rising portions of both pulse waves with each other, and multiplex both pulse waves to compare the bottoms of both wave pulses. FIG. 20 is a view explaining in detail the comparison between the forward pulse wave Wf3 and the rear pulse wave Wb3 in FIG. 19. The rear pulse wave Wb3 is delayed with respect to the forward pulse wave Wf3 by a time dt. But the forward pulse wave Wf is moved to a pulse wave Wf3' so as to agree the rising parts, and the bottoms of the pulse wave Wf3' and the pulse wave Wb3 are compared. In this embodiment, only the parts of the pulse waves below the dicroticnotch pressure DNP as the bottoms are compared with each other. In the example of FIG. 20, the parts of the waveforms below the dicroticnotch pressure are in perfect agreement with each other. Actually, however, such perfect agreement cannot be expected. Then it is preferable that the agreement with a precision below a set error (e.g., ±3%) is judged agreement. When the CPU 430 judges waveforms agreement, the CPU 430 stops for some time the leaking operation of the leak valve 450 to maintain the reference internal pressure at this time for some time. The rear pulse wave at this time is detected as the approximate aortic wave. In the example of FIG. 20, the rear pulse wave Wb3 is the approximate aortic wave. The systolic pressure SP, the diastolic pressure DP and the dicroticnotch pressure DNP can be obtained from this approximate aortic pulse wave.

2.5 Detection Result of Approximate Aortic Wave

Lastly, the approximate aortic wave detected by this apparatus is shown in FIGS. 21 and 22. FIG. 21 shows the pulse wave of a normal person. FIG. 22 shows the pulse wave of a heart diseased person. Wf6 and Wf7 represent forward pulse waves; Wf6' and Wf7', the forward pulse waves moved by a delay time dt; and Wb6 and Wb7, rear pulse waves, i.e., the approximate aortic wave. The thus obtained aortic wave agrees with the aortic wave invasively measured by the conventional blood vessel catherter method. Actual measured blood pressure values are taken on the vertical axis, and actual time values are taken on the horizontal axis. It is a characteristic that not only waveforms of pulse waves, but also blood pressure values can be simulataneously obtained non invasively. It is very useful to the synthetic judgement of heart diseases to know blood pressure values together with pulse waveforms.

2.6 Variations

Thus, this invention has been explained by means of one embodiment, but this invention is not limited to the embodiment. In short, this invention is based on the finding of the basic principle that the cuff is put around an upper arm, and when a pressure corresponding to the diastolic pressure DP is applied to the cuff, a pulse wave approximate to the aortic wave can be obtained at the upper arm. In order to recognize that a pressure of the cuff has reached the diastolic pressure DP, it is judged whether or not the lower waveforms of a forward and a rear pulse waves have agreed with each other. Accordingly, as long as the pulse wave detection based on this basic principle is possible, apparatuses of any constitutions may be used. In the above described embodiment, the parts of the pulse waves below the diastolic pressure DP are used as the lower waveforms to be compared, but different waveforms may be used as the lower waveforms to be compared. For example, lower halves of the peak values may be used. In short, what is intended by the comparison of the lower waveforms is to compare parts of the waveforms except the high frequency componens cut off by clearing the blood flow shutting bag. Which parts of the waveforms to be compared is optionally selected depending on designs.

Furthermore, another method for recognizing that the cuff has reached the diastolic pressure DP will be explained. This method is hinted by the graph of FIG. 18. In this graph, in the six waveforms (D, E, F to G) from the left, the peaks of the rear pulse waves depicted by the solid line increase along the auxiliary line S1, and those of the forward pulse waves depicted by the broken line decrease along the auxiliary line S2. But the seventh waveform from the left and its followers do not follow the linear increase and the decrease along the auxiliary lines. In other words, the linear increase and the linear decrease are maintained until the reference internal pressure reaches the diastolic pressure DP. Then it is possible to decrease the reference internal pressure, monitoring changes of the peak values of the solid line rear pulse wave or the broken line forward pulse wave in the graph, and, when a change deviating from the linear increase or the linear decrease is found, to recognize an immediately preceding pressure as the diastolic pressure DP.

As described above, according to this apparatus, a cuff having three bags is put around an upper arm to detect an approximate aortic wave. Consequently an approximate waveform of an aortic wave, and pressure values can be non invasively measured.

§3 Pulse Wave Change Detecting Apparatus 3.0 Basic Principle

The embodiment disclosed in §3 is a pulse wave change detecting device relating to the seventh and the eighth features of the present invention. By the use of the apparatuses disclosed in §1 and §2, it is possible to put the cuff around an upper arm to non invasively detect pulse waves. In the pulse wave change detecting apparatus which will be described here, a plurality of pulse waveforms detected by a pressure sensor are stored. These pulse waveforms are displayed, multiplexed on one sheet of chart. They are so multiplexed that the rising times of the respective waveforms agree with one another. Thus, transient changes of pulse waves can be visually recognized easily as distribution widths of the pulse waves. The information which part of a pulse wave is wider or narrower can be obtained at sight, and consequently more accurate diagnoses can be made.

3.1 Multiplex Recording of Pulse Wave

Figure 23:
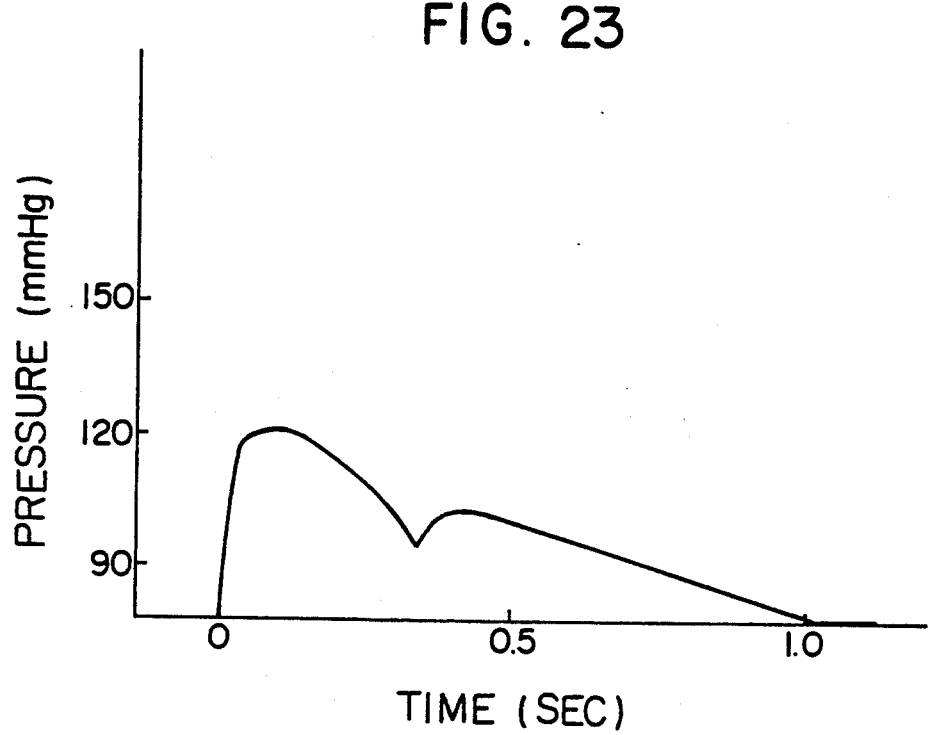
FIG. 23 is a waveform view of a single approximate aortic pulse wave.
Figure 24A:
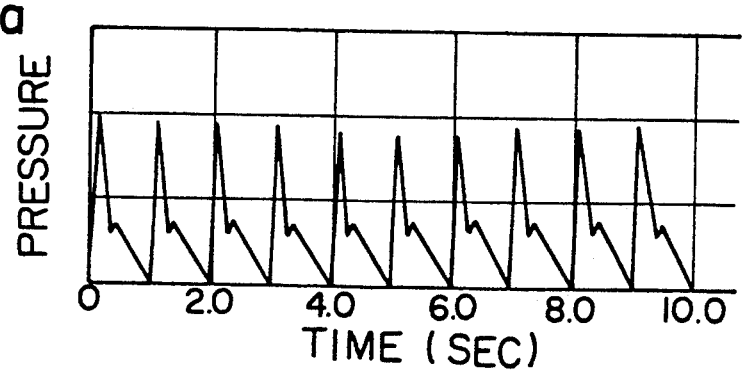
FIG. 24a is a chart of a normal person's approximate aortic waves obtained by 10-time-detections with the time axis compressed.
Figure 24B:
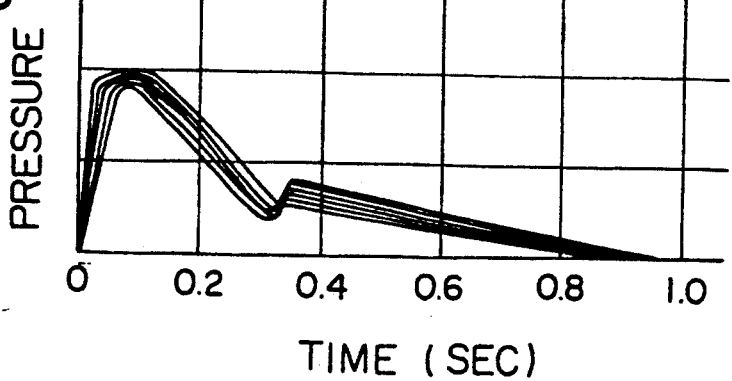
FIG. 24b is a chart of the same multiplexed pulse waves obtained by the 10-time-detections.

The constitution of the pulse wave change detecting device described here is basically the same as the pulse wave detecting device (FIG. 1) disclosed in §1 and that (FIG. 13) disclosed in §2. As described above, in these apparatuses, the waveforms of a plurality of approximate aortic waves can be measured between Point F and Point G in FIG. 16a and stored in the memory 160 or 460. But the apparatus described here has the function that the CPU 130 or 430 outputs to the printer 180 or 480 these approximate aortic waveforms multiplexed. FIG. 23 shows a chart of the case that one of the approximate aortic wave is singly outputted. From this chart, its waveform can ge fully analyzed, but its transient changes cannot be analyzed. In this device, based on the data of the memory 160 or 460, the charts of FIGS. 24a and 24b are outputted to the printer 180 or 480. FIG. 24a shows waveforms obtained by consecutive 10 time detections with the time axis of the chart of FIG. 23 compressed. Since the time axis is compressed, it is difficult to analyze the shapes of the respective waveforms, but their transient information can be obtained. FIG. 24b shows a display of waveforms which is a point of this invention. This is a chart of multiplexed pulse waves obtained by consecutive 10 time detections with the time axis not compressed. The waveforms for 10 time detections are multiplexed with their rising times set at 0 of the time axis. By thus displaying pulse waves multiplexed, changes of the pulse waves can be visually recognized in a distribution width of a plurality of graphs. In this device, the CPU 130 or 430 reads out pulse wave data stored in the memory 160 or 460 for 10 times, forms a chart of FIG. 24a and that of FIG. 24b, and outputs these charts to the printer 180 or 480.

3.2 Pulse Wave Change Detection Result

Figure 25A:
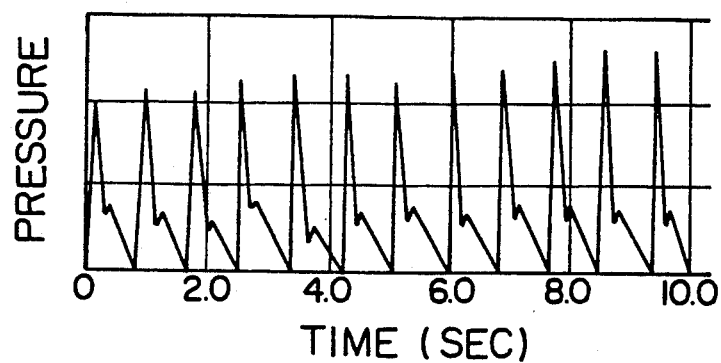
FIG. 25a is a chart of approximate aortic waves of a young patient with a blood circulatory disease detected by 10-time-detections with the time axis compressed.
Figure 25B:
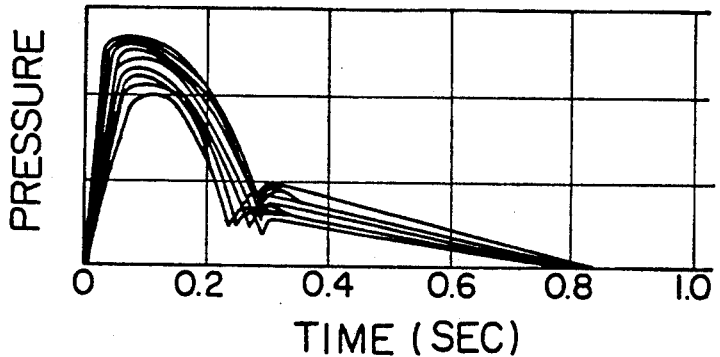
FIG. 25b is a chart of the same multiplexed pulse waves detected by the 10-time-detections.
Figure 26A:
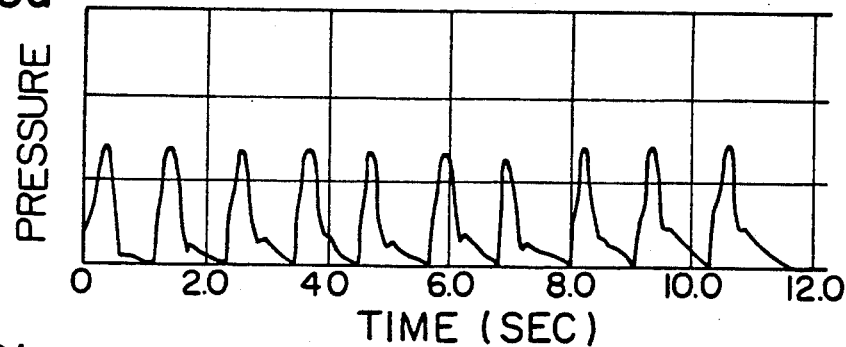
FIG. 26a is a chart of approximate aortic waves of an old patient with a circulatory system disease detected by 10-time-detections with the time axis compressed.
Figure 26B:
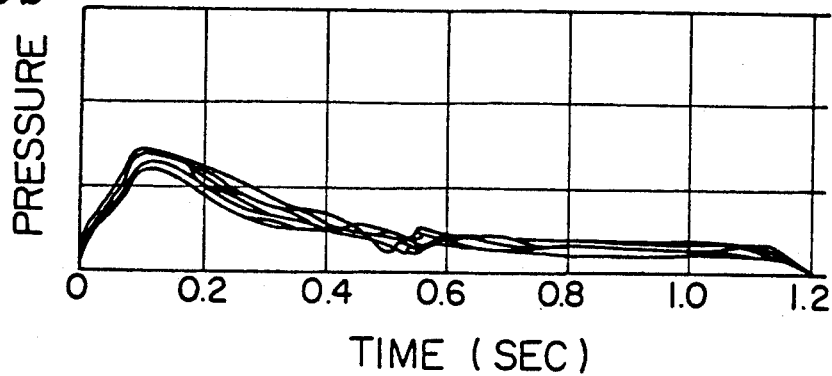
FIG. 26b is a chart of the same multiplexed pulse waves detected by the 10-time-detections.

The charts of FIG. 24a and FIG. 24b show the waveforms of aortic waves of a normal person. FIGS. 25a and 25b, and FIGS. 26a and 26b show the waveforms of aortic waves of a diseased person. The charts of FIGS. 25a and 25b show pulse waves of a young patient with a blood circulatory disease. The charts of FIGS. 26a and 26b show pulse waves of an old patient with a circulaton system disease. In FIG. 25a, considerable transient changes are found at pulse wave peaks at 0.05 to 0.1 seconds on the time axis, the dicroticnotch pressure, and the shutting time. On the other hand, in FIG. 26b, it is found that the falling waves, and the dicroticnotches at 0.5 seconds on the time axis deviate with respect to the time axis. Thus, the detection result of this device enables not only the waveforms of pulse wave, but also their transient changes to be easily seen. That is, this device can provide extra information for accurate diagnoses. The charts of FIGS. 24a to 26b show pulse waves only in graphs, but pressure values of respective parts may be also indicated in numerical values. For example, for the pulse waves for 10 time detections, a maximum value, a minimum value and average value of a peak value at the systolic pressure may be also indicated in numerical values, and if their values are outside their normal ranges, some warning marks may be indicated.

As described above, this apparatus displays a plularity of pulse waves multiplexed. Consequently transient changes in pulse waves can be visually recognized with ease.

§4 Pulse-Wave/Arterial-Sound Composite Recording Apparatus 4.0 Basic Principle

The embodiment disclosed in §4 is a wave-pulse/arterial-sound composite recording device related to the 9th to 14th features of the present invention. This apparatus is a development of the pulse wave detecting device disclosed in §1. In the device (FIG. 1) disclosed in §1, the sound wave sensor 110 detects arterial sounds (Korotkoff sounds), and the sensor 120 detects pulse waves. In this apparatus, the CPU 130 synthesizes a pulse wave and an arterial sound to output the result to a printer 180. This apparatus has the following six characteristics which correspond respectively to the ninth to the fourteenth features.

According to the first characteristic of this apparatus, pressure values are taken on the vertical axis, and time is taken on the horizontal axis, whereby a pulse wave and an arterial sound are compositely indicated on the same time axis. Furthermore, the high pressure period before the dicroticnotch, and the low pressure period following the same are indicated separately. Consequently information necessary for the diagnosis of circulatory organ diseases can be visually obtained with ease.

According to the second characteristic of this apparatus, standard lines for trisecting the part of the time axis for the high pressure period, and standard lines for bisecting the part of the time axis for the low pressure period are outputted. The information in the three sections of the high pressure period indicate respectively information of the circulatory system associated with the heart, the lung, the gastrointestines (digestive organs), and the information in the two sections of the low pressure period indicate respectively information of the circulatory system associated with the liver, and the kidney. Consequently more elaborate diagnoses can be performed.

According to the third characteristic of this apparatus, the standard envelope of the Korotkoff sounds is indicated. Consequently deviations of a specific patient's measurement result from the standard result can be visually recognized with ease.

According to the fourth characteristic of this device, Korotkoff sounds in the period from the low pressure period to the so called Point K4 to K5 are indicated. Consequently more information which is usefully available to diagnoses can be visually recognized.

According to the fifth characteristic of this apparatus, measurement results on the left and the right sides of a body are indicated in line symmetry. Consequently the left half and the right half of a patient's body can be separately diagnosed.

According to the sixth characteristic of this apparatus, pulse waves can be measured non invasively. That is, by means of the pulse wave detecting device disclosed in §1 is used as it is, the measurement can be made only by putting the cuff around an upper arm.

4.1 Pulse-Wave/Arterial-Sound Composite Recording

The constitution of the pulse-wave/arterial-sound composite recording apparatus, which will be disclosed here, is basically the same as the pulse wave detecting device (FIG. 1) disclosed in §1. As described above, between Points F and G in FIG. 5a a plurality of approximate aortic pulse waves are measured, and Korotkoff sound waveforms corresponding to the period between Points D and H in FIG. 5a are measured. In the apparatus which will be described here, these pulse waves and Korotkoff sounds are stored by the memory 160, and later the CPU 130 synthesizes them to output a synthesized result to the printer 180.

Figure 27:
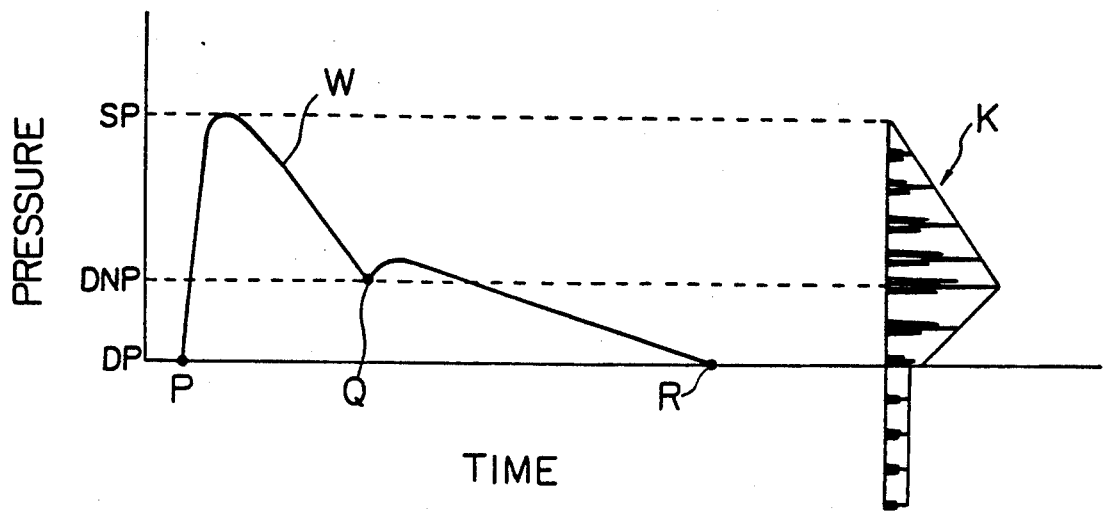
FIG. 27 is a waveform view of approximate pulse waves and arterial sounds detected by the apparatus of FIG. 1.

First, the CPU 130 averages the approximate aortic waves stored in the memory 160 to obtain an average pulse wave. The waveform W in FIG. 27 is the thus obtained average waveform. The absolute values of pressures are taken on the vertical axis of the average waveform, and the maximum value is a systolic pressure SP, and the minimum value is the diastolic pressure DP. Time (second) is taken on the horizontal axis. The waveform of Korotkoff sounds K corresponding to pressure values as on the right side of FIG. 27 is stored in the memory 160. This waveform is that of Korotkoff sounds detected at the points after Point D in the measuring operation of FIG. 5a and stored together with the pressure values. In this embodiment, a waveform of Korotkoff sounds is outputted by a half amplitude. In FIG. 27 the waveform is shown by a half amplitude. The CPU 130 outputs to the printer the waveform of the Korotkoff sounds K, and the waveform of the average pulse wave W as follows.

First, the position of a dicroticnotch is recognized based on the average pulse waves W. This Point Q can be recognized by computation as the point where, for example, a sign of a differential coefficient of the averate pulse wave W changes. In aortic insufficiencies, results having a plurality of Point Q are obtained. In these cases, the latest Point Q on the time axis is used. When the position of Point Q is thus determined, a dicroticnotch pressure DNP can be given as the ordinate of Point Q. Point P where the average pulse wave W rises, and Point R where the average pulse wave terminates can be given by computation.

Figure 28:
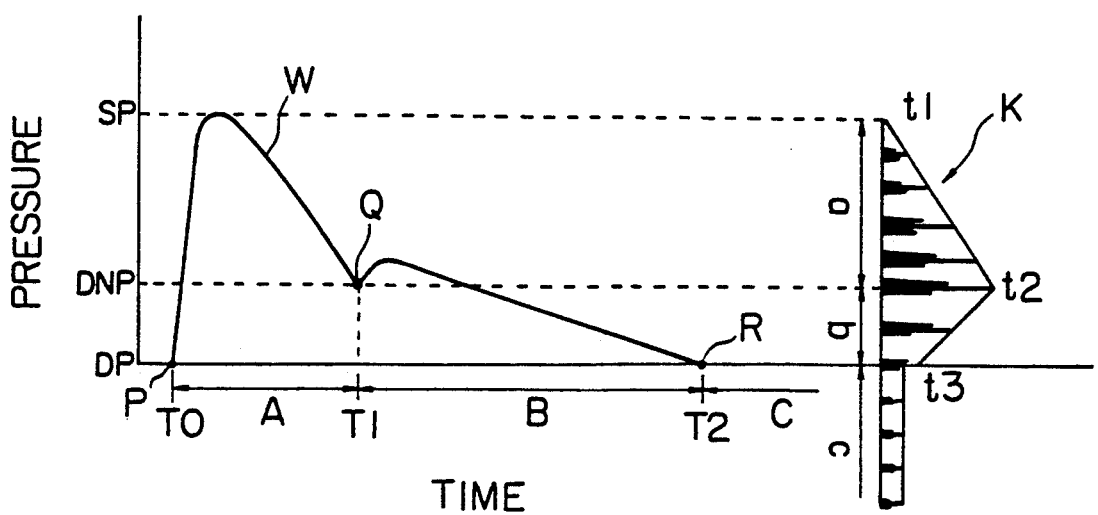
FIGS. 28 and 29 are views explaining a processing for a display of the approximate aortic waves with the arterial sounds multiplexed thereon on the waveform view of FIG. 27.
Figure 29:
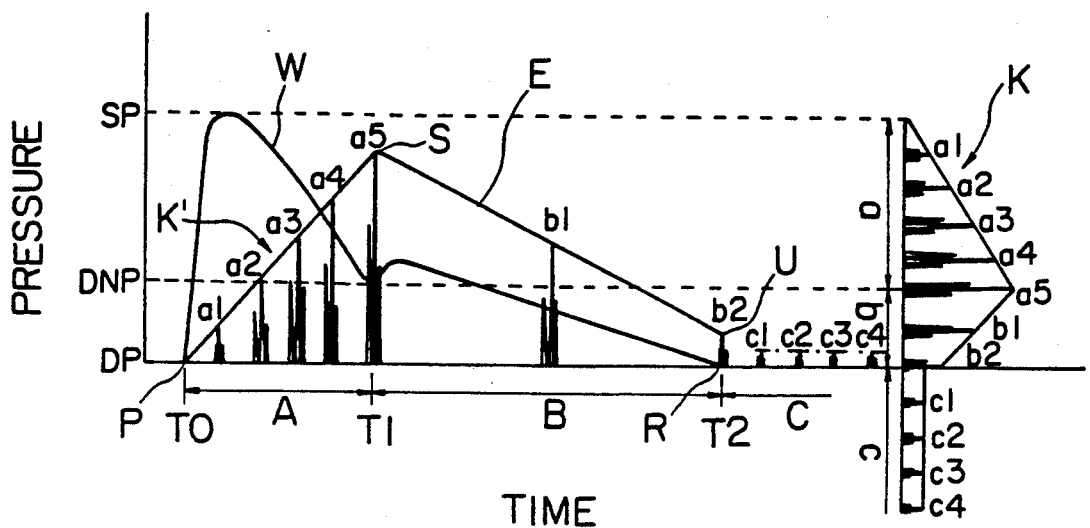

When the three Points P, Q and R are determined, as shown in FIG. 28, the time axis (horizontal axis) is devided at these three points. The abscissas of Points P, Q and R on the time axis are T0, T1 and T2 respectively. The section between Time Points T0 and T1 is a high pressure period A, the section between Time Points T1 and T2 is a low pressure period B, and the period after Time Point T2 is the third period C. On the other hand, the Korotkoff sounds K are divided along the pressure axis (vertical axis) as shown on the right side of the FIG. 28. That is, the section between the systolic pressure SP and the dicroticnotch pressure DNP is a high pressure period a, and the section between the dicroticnotch pressure DNP and the diastolic pressure DP is a low pressure period b, and the period after the diastolic pressure DP is the third period c. Then, the pressure axis of the Korotkoff sound wave form in the high pressure period a is linearly applied to the time axis of the average pulse wave in the high pressure period A. The pressure axis of the Korotkoff sound waveform in the low pressure period b is linearly applied to the time axis of the average pulse wave in the low pressure period B, whereby the Korotkoff sound waveforms of the respective periods are displayed, superposed on the average pulse wave. FIG. 29 shows this result. The waveform of the Korotkoff sounds a1 to a5 are displayed, superposed on the average pulse wave W so that the section of the high pressure period a agrees with the section of the high pressure period A, and the Korotkoff sound waveform b1, b2 are displayed, superposed on the average pulse wave W so that the section of the low pressure period b agrees with the section of the low pressure period B.

The Korotkoff sounds K' are displayed with the amplitudes enlarged by multiplying the amplitudes with a set coefficient for easier view. Since the high pressure period and the low pressure period are separately treated, the interval between adjacent Korotkoff sound waveforms is smaller in the high pressure period, and is wider in the low pressure period. Since the third periods C and c are not restricted, the Korotkoff sound waveforms c1 to c4 in the third period c are displayed in the third period C at an arbitrary interval on the time axis of the average pulse wave W.

Furthermore, in this embodiment, a standard envelope E of the Korotkoff sounds K' as shown in FIG. 29 is displayed. In this embodiment, this envelope E is given by connecting Point P, Point S at the peak of the Korotkoff sound waveform a5 at the boundary time point T1 between the high pressure period A and the low pressure period B, Point U of the Korotkoff sound waveform b2 at the boundary time point T2 between the low pressure period B and the third period C. It is known that the peaks of the respective waveforms of Korotkoff sounds K', in the measurements of general normal people, are on the envelope E. It is possible to diagnose abnormalities, based on how much the peaks are deviated from the envelope E. The method for determining the envelope E is not limited to the above described method, and various methods can be considered. It is possible to use, for example, an average of envelopes given by measurements of some normal people as the standard envelope E.

4.2 Applications to Diagnoses

Figure 30:
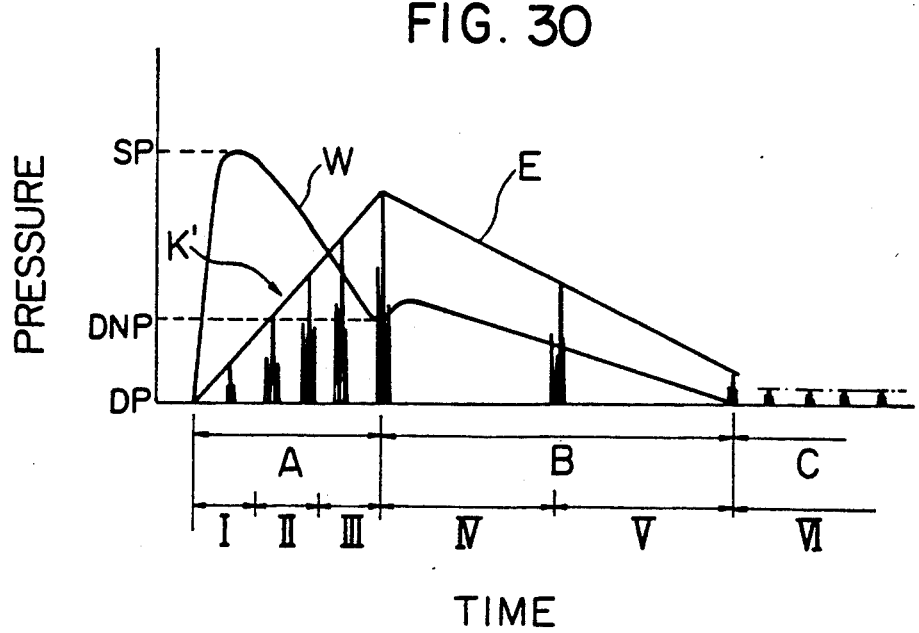
FIG. 30 is a view of a result of the composite recording based on the waveform view of FIG. 27.

The CPU 130 prepares the graph of FIG. 30 by the above described computation, and outputs this graph to the printer 180 to display a measurement result. Diagnosticians can obtain various information of patients' circulatory diseases, based on the output result, as of FIG. 30, of the printer. One characteristic of this output result is that the waveform of approximate aortic waves are recorded as an average pulse wave W, and the approximate aortic pulse wave W is depicted with the absolute values of pressures taken on the vertical axis, and absolute values of time taken on the horizontal axis. That is, the absolute values of blood pressures can be confirmed together with waveforms of approximate aortic waves. Another characteristic is that the waveforms of arterial sounds (Korotkoff sounds K') are recorded together with the approximate aortic waves. The waveforms of arterial sounds are recorded at specific positions on the time axis by the above described processing. The recording position of the arterial sound waveforms on the time axis is very significant as information for diagnoses. This significance will be explained below.

In FIG. 30, the high pressure period A represents the process in which the heart contracts to send out blood to the aorta, and the aortic valve closes. That is, the high pressure period A is a part represents the dynamic movement of the heart. The low pressure period B represents the process following the closure of the aortic valve and does not show the movement of the heart itself. Then the flow of the blood sent out from the heart to the aorta will be followed. After sent out from the heart, the blood flows gradually from the arteries to the periphery, i.e., to the center, the lung, the gastrointestines (digestive organs), the liver, the kidney, and to the veins and back to the heart. The inventive finding made by the inventor of the present application is the fact that pulse waves and arterial sound waveforms arranged together with the pulse waves as shown in FIG. 30 indicate information of circulatory system troubles corresponding to this blood flow. This fact will be explained in more detail. As shown in FIG. 30, the section of the high presure period A is trisected in Sections I, II, III. The section of the low pressure period B is bisected in Sections IV, V. The section of the third period is Section VI. The arterial sound waveforms in the respective sections have information of circulatory troubles of specific parts of a patient. Specifically, the inventor of the present application has recognized that the waveform of the Korotkoff sound K' belonging to Section I has information of the heart blood flow. The waveform of the Korotkoff sound K' belonging to Section II has the information of the blood flow of the lung. The waveform of the Korotkoff sound K' belonging to Section III has the information of the blood flow of the stomach and the intestines (digestive organs). The waveform of the Korotkoff sound K' belonging to Section IV has the information of the blood flow of the liver. The waveform of the Korotkoff sound K' belonging to Section V has the information of the blood flow of the kidney. The waveform of the Korotkoff sound K' belonging to the third period C (Section VI) is Korotkoff sounds in the regions generally called K4 Point to K5 Point and is considered to have the information of the bladder, the legs, which are more peripheral than the kidney, and the head. So far this fact has not been theoretically discussed, but based on this fact, it has been long practiced to diagnose circulatory diseases of the parts by feeling pulses of patients.

4.3 Detection Result of Pulse-Wave/Arterial-Sound

Figure 31:
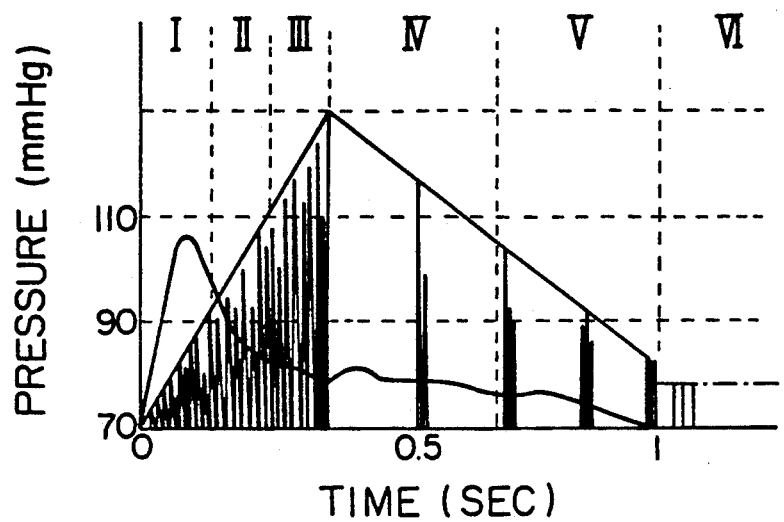
FIG. 31 is a graph of an output result of the printer involved in the apparatus of FIG. 1.

FIG. 31 is the graph showing the result of an actual measurement on a normal person, using the pulse-wave/arterial-sound composite recording device according to this embodiment. Actually as shown in the graph, the arterial sound waveforms are dense in the high pressure period (Sections I, II, III) and is rare in the low pressure period (Sections IV and V). In this embodiment, to clarify the respective sections, standard lines (broken vertical lines in the graph) for trisecting the high pressure period and for bisecting the low pressure period are shown. Standard lines (broken horizontal lines in the graph) for indicating amplitudes of arterial sound wave are also shown. It is possible to discriminate the information of circulatory system troubles diseases associated with the above described parts, based on these standard lines.

Figure 32:
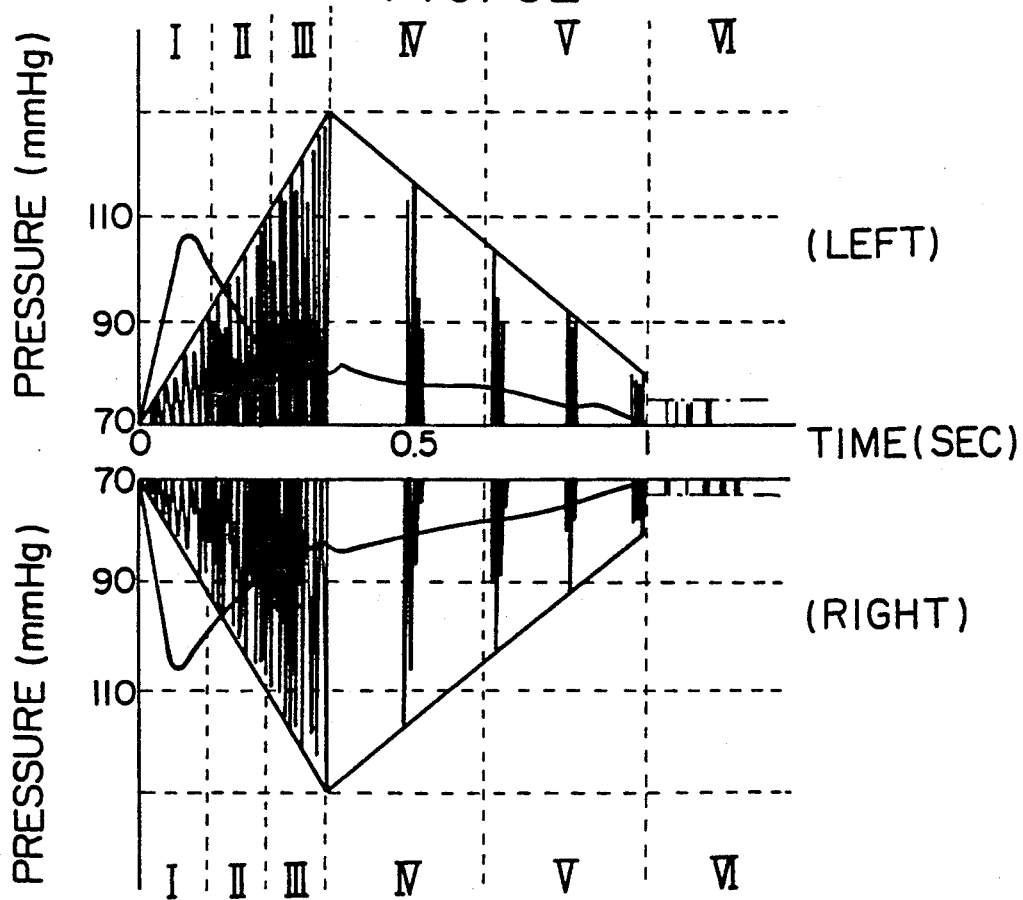
FIG. 32 is a view of an output of a measurement result of the apparatus of FIG. 1 on both upper arms on the printer.

FIG. 32 contains the graphs showing the results of the measurement made by the cuff put around the left and right upper arms of a normal person, using the pulsewave/arterial-sound composite recording device, and the graphs showing the results of the measurement made by the cuff put around his left and right upper arms, using the same device, both graphs being symmetrical to a line along a time axis. The upper half graph is of the measurement result of the left upper arm, and the lower half graph is the of measurement result of the right upper arm. It is considered that the measurement result of the left upper arm indicates the information of the left half body, and the measurement result of the right upper arm indicates the information of the right half body. Resultantly, by showing both graphs along the same time axis, conveniently the conditions of a total body can be seen at sight. With respect to the head center, the left and the right information is reverse.

Thus this invention has been described by means of embodiments but is not limited to the embodiments. In short, the essence of this invention is that pulse waves are divided in the high pressure period and the low pressure period along a dicroticnotch, and the pressure axis of arterial sounds is linearly applied to the time axes of the respective periods so that the waveforms of the pulse waves, and the arterial sounds are displayed on the same time axis. This invention can be practiced in various forms.

According to a first characteristic of this apparatus, blood pressure values are taken on the vertical axis, time being taken on the horizontal axis, and pulse waves and arterial sounds are compositely displayed on the same time axis and furthermore separately in the high pressure period before a dicroticnotch, and in the following low pressure period. Consequently information for the diagnosis of circulatory system diseases can be visually seen easily at sight.

According to a second characteristic of this apparatus, standard lines for trisecting the time axis of the high pressure period, and for bisecting the time axis of the low pressure period are outputted. Consequently information in the three sections of the high pressure period can be recognized as information respectively of the circulatory system associated with the heart, the lung and the gastrointestines (digestive organs), and information in the two sections of the low pressure period can be recognized as information respectively of the liver and the kidney. More detailed diagnoses can be performed.

According to a third characteristic of this apparatus, the standard envelope of Korotkoff sounds is displayed. Consequently it is possible to visually recognize easily deviations of the measurement result of a specific patient from the standard measurement result.

According to a fourth characteristic of this apparatus, Korotkoff sounds are displayed to the so called Points K4 to K5 following the low pressure period. Consequently it is possible to visually recognize more information useful to diagnoses.

According to a fifth characteristic of this apparatus, the left and the right measurement results are displayed symmetrically along a line. Consequently the left and the right haves of a patient's body can be separately diagnosed.

According to a sixth characteristic of this apparatus, pulse waves and arterial sounds are measured by the cuff. Consequently the above described diagnoses can be performed non invasively.

§5 Blood Circulatory Information Display Apparstus

5.0 Basic Principle

The embodiment disclosed in §5 is the blood circulatory information display apparatus relating to the 15th to 17th features of the present invention. This apparatus is a development of the pulse-wave/arterial-sound composite recording apparatus disclosed in §4. In this apparatus, an envelope of arterial sound waveforms (Korotkoff sounds), and pulse waves are displayed in a diagram, concurrently parts with blood circulation troubles being indicated by icons of the human body. This apparatus has the following three characteristics, and these characteristics correspond respectively to those of the 15th to 17th features.

According to a first characteristic of this apparatus, blood pressures are taken on the vertical axis, and time is taken on the horizontal axis. Pulse waves, and two envelopes are compositely displayed on the same time axis. The first envelope connects points at maximum peaks of Korotkoff sound waveforms, and based on a contour of this envelope, general information of blood circulation troubles are obtained. The second envelope connects points at second peaks of the Korotkoff sound waveforms. Based on a contour of this envelope, information of levels of blood circulation troubles are obtained. By thus displaying these two envelopes together with pulse waves, information for diagnoses of circulatory troubles can be visually obtained.

According to a second characteristics of this invention, three icons representing the human body are displayed. A first icon indicates a reference position. A second icon can change its display position, based on a Korotkoff sound waveform obtained from the cuff put around a right upper arm to indicate the level of a blood circulation trouble in the right half of the body. A third icon can change its display position, based on a Korotkoff sound waveform obtained from the cuff put around on the left upper arm to indicate level of circulation troubles in the left half of the body. Thus, it is possible to visually see the levels of circulatory organ diseases separately in the left and the right halves of a body.

According to a third characteristic, in comparison of an envelope of Korotkoff sound waveforms with a reference envelope, when a gap between the two envelopes exceeds a set limit, the judgement that there is a circulatory disease. Furthermore, since it is possible for the time axis of the graph to correspond to parts of the human body, part of circulatory diseases can be specifically displayed.

5.1 Basic Structure of the Apparatus

Figure 33:
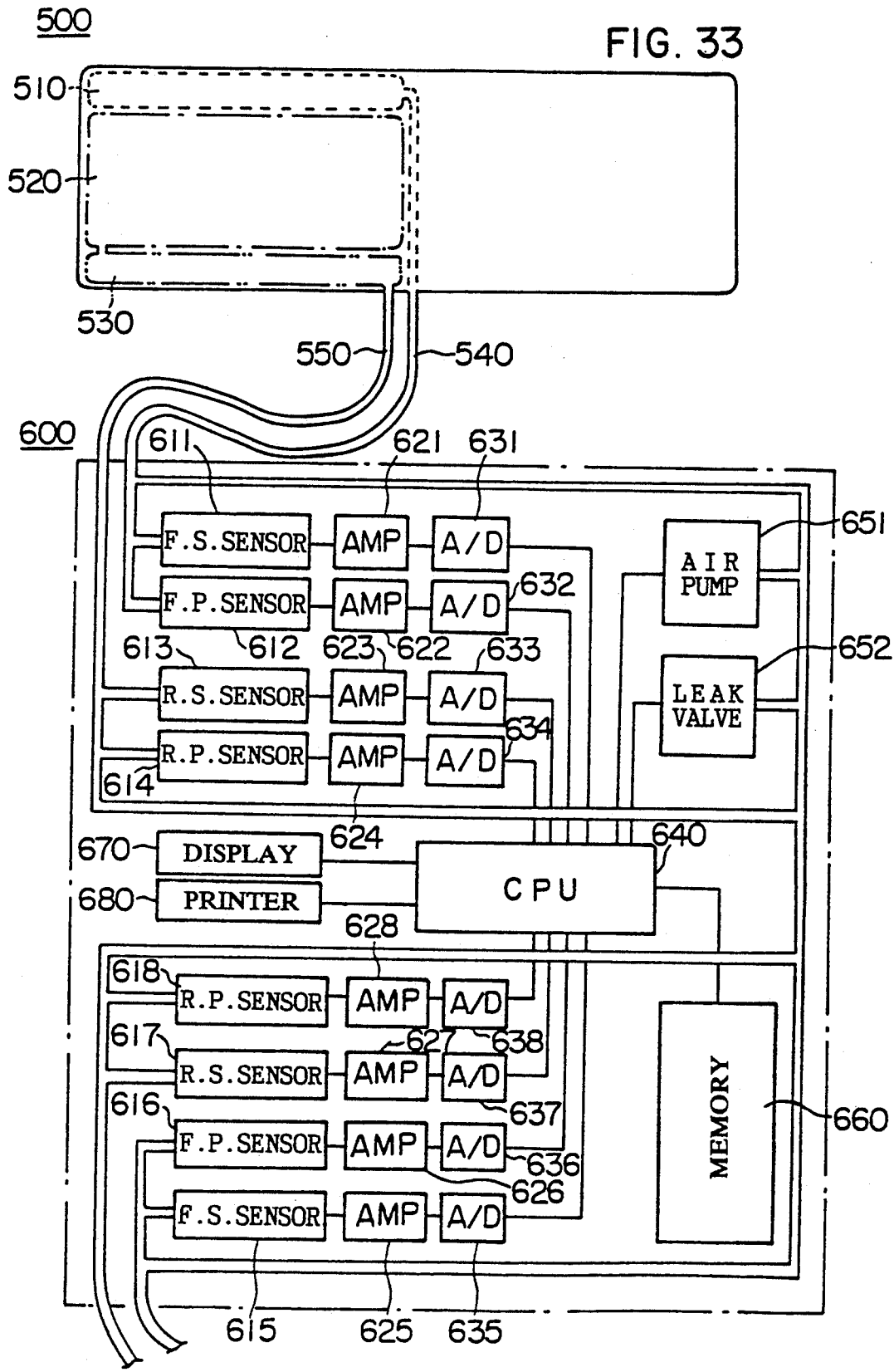
FIG. 33 is a block diagram of a structure of a blood circulatory information display apparatus according to a third embodiment of this invention.
Figure 34:
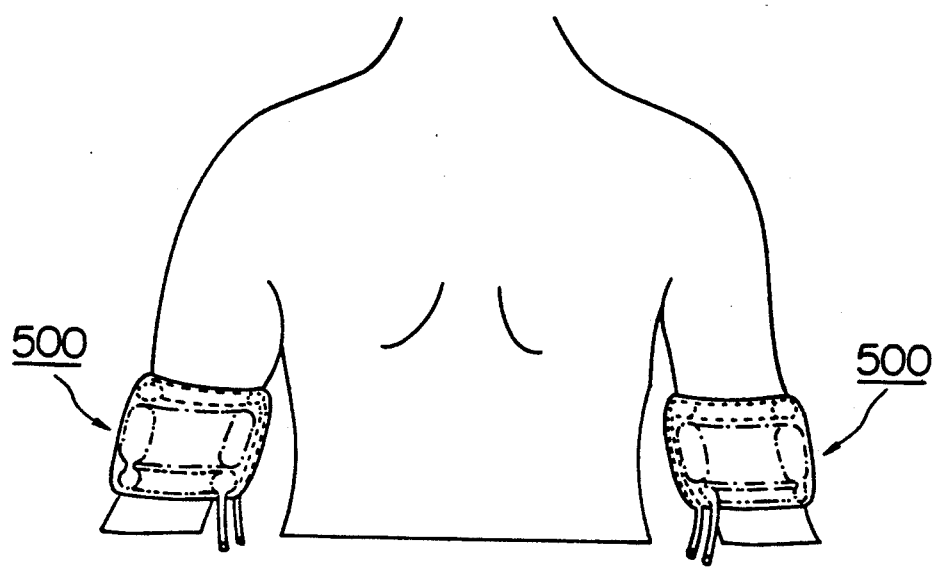
FIG. 34 is a view of a state of a cuff involved in the apparatus of FIG. 33 in which the cuff is put around both upper arms.

FIG. 33 is a block diagram of the basic structure of the blood circulation information display apparatus according to one embodiment of this apparatus. This apparatus is largely divided in a apparatus body 600 (enclosed by the one dot chain line), and a pair of cuffs 500 (the other of the cuffs to be connected to the apparatus body 600 at the lower part of the drawing is not shown). The cuff 500 is quite the same as that in FIG. 13 (§2). The apparatus body 600 has substantially the same structure as the apparatus of FIG. 13, but some of the constituent elements are provided in pairs so that information can be collected concurrently from the left and the right upper arms. There are provided a CPU 640, a memory 660, a display 670, a printer 680, an air pump 651, and a leak valve 652. The remaining elements are provided each in tow pairs respectively on the upper and the lower sides of the drawing of the apparatus body. For example, when the cuff 500 shown on the upper side of the drawing is put around a right upper arm, and the not shown cuff (connected at the bottom of the drawing) is put around on the left upper arm, the elements shown on the upper side of the drawing of the apparatus body collects information from the right upper arm, and the elements shown on the lower half of the drawing of the apparatus body collect information from the left upper arm. FIG. 34 shows the state of a pair of cuffs put around both upper arms.

In FIG. 33 at the upper half of the drawing of the apparatus body a forward sound wave sensor 611, a forward pressure sensor 612, a rear sound wave sensor 613 and a rear pressure sensor 614 are shown. These sensors are for detecting pressure changes or Korotkoff sound generated in a forward bag 510 and a rear bag 530. Signals from the respective sensors are amplified by amplifiers 621 to 624, and are digitized by A/D converters 631 to 634 to be supplied to the CPU 640. The reference internal pressures of the cuff 500 and another cuff not shown are controlled by actuating the air pump 651 and the leak valve 652. Quite the same structure is shown on the lower half of the drawing of the device body. Signals from sensors 615 to 618 are amplified by amplifiers 625 to 628 to be digitized by A/D converters 635 to 638 to be supplied to the CPU 640. Thus, the reference internal pressures of the pair of cuffs put around a left and right upper arms can be concurrently controlled to be the same.

5.2 Basic Operation of the Apparatus

This apparatus can make not only the measurement by the apparatus according to the first feature (§1) of the present invention shown in FIG. 1, but also the measurement by the apparatus according to the second feature (§2) of the present invention shown in FIG. 13. That is, the rear sound wave sensors 613, 617 are used as the sound wave sensor 110 in FIG. 1, and the rear pressure sensors 614, 618 are used as the pressure sensor 120 in FIG. 1, whereby this device can make the same function as the apparatus of FIG. 1. The forward pressure sensors 612, 616 are used as the forward sensor in FIG. 13, and the rear pressure sensors 614, 618 are used as the rear sensor in FIG. 13, whereby this apparatus can make the same function as the apparatus of FIG. 13. The forward sound wave sensors 611, 615 are not used in practicing this inventions, but it is possible to cause this apparatus to function as the arterial distensibility measuring apparatus disclosed in U.S. patent application Ser. No. 07/521156 or EPO Patent Application No. 90109281.7 by using output signals from the forward sound wave sensors 611, 615.

In this apparatus, Korotkoff sounds are obtained as outputs of the rear sound wave sensors 613, 617. Pulse waves approximate to aortic waves can be obtained as outputs of the rear pressure sensors 614, 618 generated when the reference internal pressure of the cuff 500 is maintained at a diastolic pressure DP. Whether or not the reference internal pressure of the cuff 500 has reached the diastolic pressure can be detected by either of two methods. A first method is the detection method (§1) using Korotkoff sounds as used in the apparatus of FIG. 1. A second method is the method (§2) for detecting an agreement of the bottom of a forward pulse wave with that of the rear pulse wave, which is conducted in the apparatus of FIG. 13. Thus, Korotkoff sound waveforms and pulse waves approximate to an aortic wave from a systolic pressure SP to a diastolic pressure DP are obtained separately from a left and right upper arms, and stored in the memory 660. The CPU 640 performs the same processing as described in §4, based on the data stored in the memory 660. That is, as described in FIG. 29, the time axis of an average pulse wave W is divided in a high pressure period A, a low pressure period B and the third period C, and Korotkoff sound waveforms are applied linearly to the respective periods, so that the pulse waves and the Korotkoff sound waveforms are complexed in a graph with the time axis in common. In the apparatus of §4, this complexed graph is outputted to the printer together with the standard envelope. But in this apparatus a little different processing is performed. That is, in this apparatus what is outputted to the printer 680 are tow charts called pulse-wave/envelopes diagram and icons/blood circulation trouble part display.

5.3 Pulse-Wave/Envelopes Diagram

Figure 35:
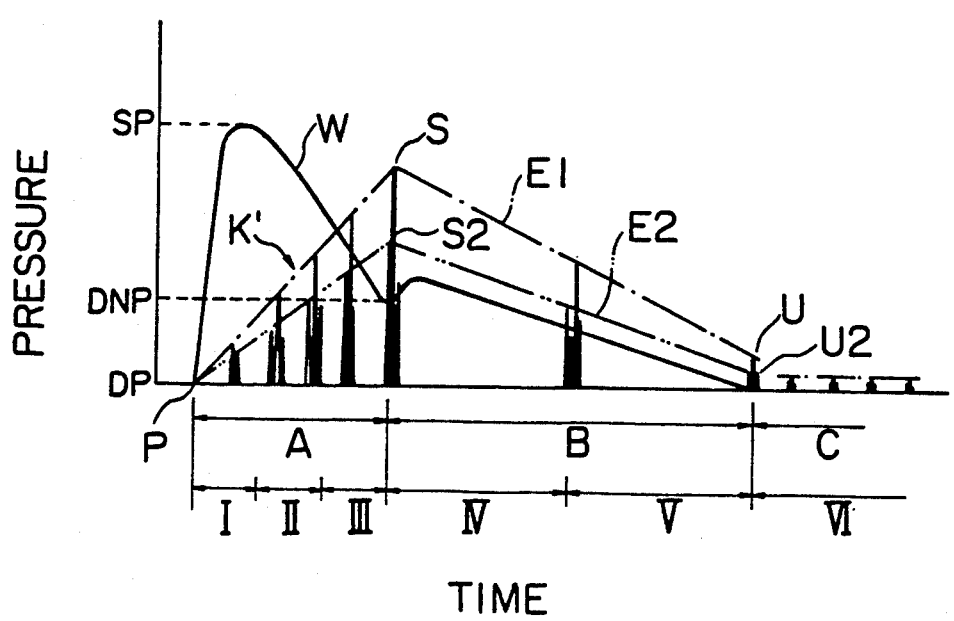
FIG. 35 is a view of approximate aortic waves and arterial sounds detected by the apparatus of FIG. 33 multiplexed on a periodic time axis of the approximate aortic waves.
Figure 36:
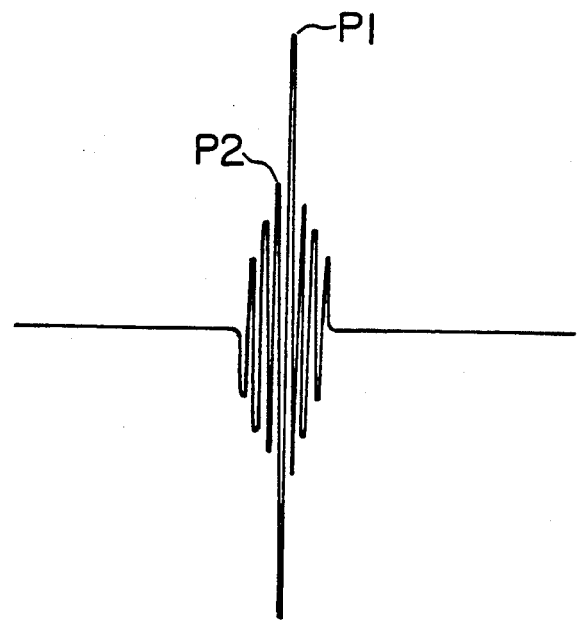
FIG. 36 is an enlarged view of a waveform of a Korotkoff sound.
Figure 37:
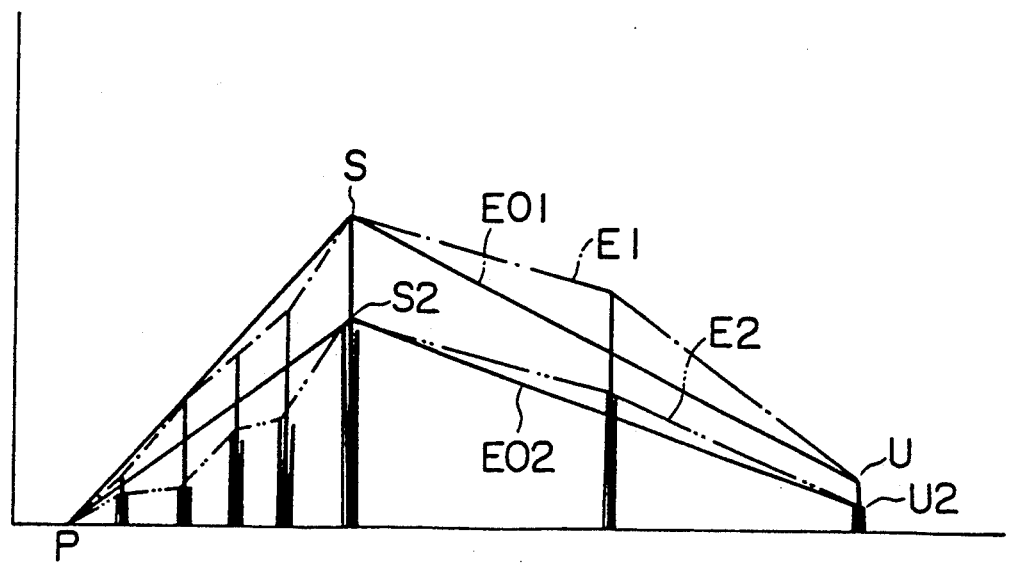
FIG. 37 is a view of two envelopes displayed by the apparatus of FIG. 33.

First, the pulse-wave/envelopes diagram will be explained. When pulse waves and Korotkoff sound waveforms are multiplexed on a graph with the time axis common, two envelopes are given on the Korotkoff sound waveforms. That is, a first envelope connects maximum peaks of the respective Korotkoff sound waveforms, and a second envelope connects second peaks of the respective Korotkoff sound waveforms. In FIG. 35, the first envelope E1 is indicated by the one dot chain line, and the second envelope is indicated by the two dot chain line. The maximum peak and the second peak of the Korotkoff sound waveform have the following meanings here. FIG. 36 is an enlarged view of one Korotkoff sound waveform (whose full amplitude is shown). The point at the maximum peak means here the point P1 at a peak which has a maximum amplitude. The point at a second peak means here P2 at a peak which has a second largest amplitude. Accordingly the first envelope E1 connects Points P1 of the respective Korotkoff sound waveforms, and the second envelope E2 connects Points P2 of the respective Korotkoff sound waveforms. These envelopes E1, E2 means a little different from the standard envelope E in FIG. 30. The standard envelope E is given in a straight line connecting three peaks, while the envelopes E1, E2 actually connect the peak positions of a plurality of Korotkoff sound waveforms as show in FIG. 37. It is known that the envelopes E1, E2 thus obtained on standard normal people well agree with the standard envelopes E01, E02. Where the standard envelope E01 connects three Points P, S and U of maximum Korotkoff sound waveforms (Point S is the position of a maximum peak of a Korotkoff sound waveform on the boundary between Sections III and IV, and Point U is the position of a maximum peak of a Korotkoff sound waveform on the boundary between Sections V and VI), and the standard envelope E02 connects three Points P, S2 and U2 (Point S2 is the position of a second maximum peak of a Korotkoff sound waveform on the boundary between Sections III and IV, and Point U2 is the position of a second maximum peak of a Korotkoff sound waveform on the boundary between Sections V and VI). That is, in FIG. 35, the envelope E1 perfectly agrees with the standard envelope E01, and the envelope E2 perfectly agrees with the standard envelope E02. Actually, however, such perfect agreement between the envelopes is a measurement result of normal people. In measurement results of patients, the envelopes much deviate from the standard envelopes. FIG. 37 shows one example of such deviations. In FIG. 37 the standard envelopes E01, E02 indicated by the solid lines, the first envelope E1 is indicated by the one dot chain line, and the second envelope E2 is indicated by the two dot chain line. In the case that actually given envlopes deviate from the standard envelopes, these deviations can be recognized as deriving from blood flow troubles of the circulatory system.

Figure 38:
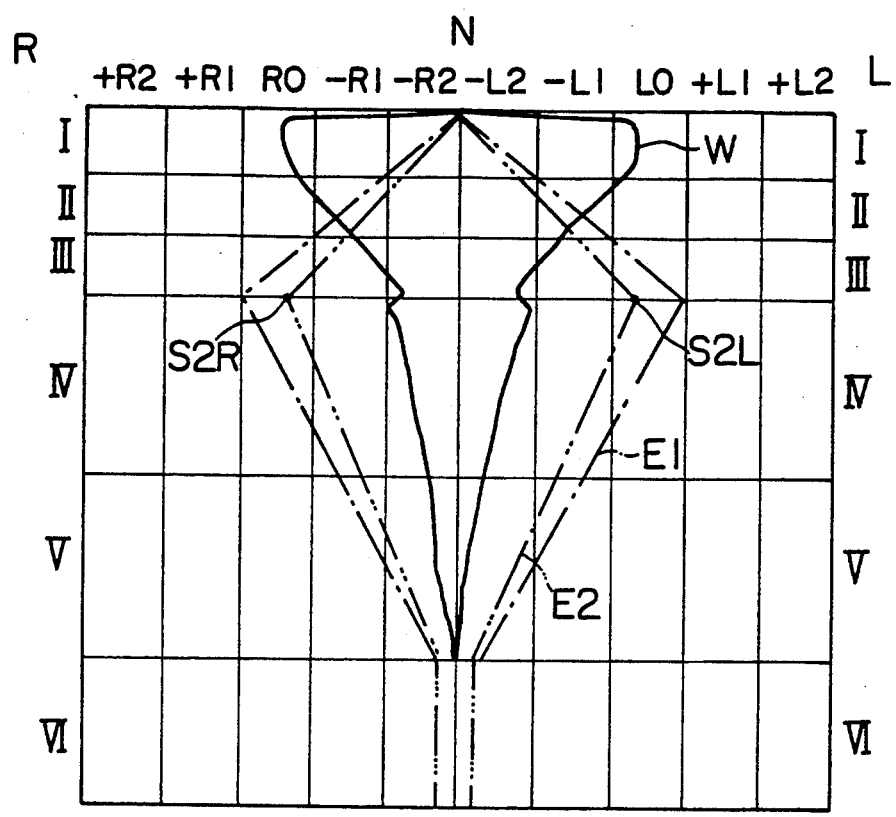
FIG. 38 is a pulse-waves/envelopes diagram displayed by the apparatus of FIG. 33.

The pulse-wave/envelope diagram of FIG. 38 is a chart in which a pulse wave and the two envelopes are shown on the same graph, and a measurement result of a normal person. In this embodiment, the pulse wave W is indicated by the solid line, the first envelope E1 is indicated by the one dot chain line, and the second envelope E2 is indicated by the two dot chain line. In Section VI, the peak value of a Korotkoff sound waveform is indicated by the three dot line. In actually outputting this chart by the printer 680, all the outputs may be displayed in solid lines. If a color printer is used, the outputs may be discriminated by colors. This chart has vertical and horizontal sectional lines. The horizontal sectional lines define Sections I to VI described in §4. The vertical sectional lines section the horizontal axis at a set interval. The horizontal axis is divided in 10 sections +R2, +R1, ... +L1, +L2. Five Sections +R2 to −R2 on the left half of the center line N in FIG. 38 is for information supplied by the cuff put around a right upper arm, and five Sections +L2 to −L2 on the right half of the center line N are for information obtained by the cuff put around the left upper arm. On the chart, R and L are reverse for the agreement with the icons/blood circulation trouble part display which will be described later. The division of the horizontal axis is preset so that the peaks S2L, S2R of the sencond envelopes of a standard normal person are located respectively in Section L0 and Section R0.

Figure 39:
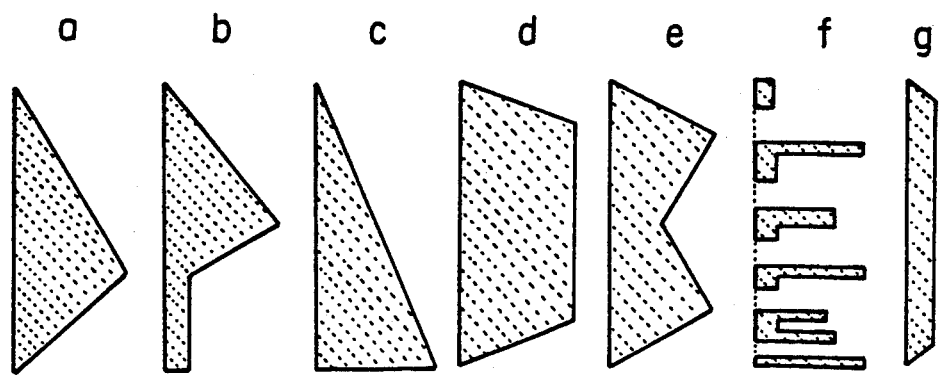
FIG. 39 is a view of examples indicative of the blood circulatory information given by a first envelope.
Figure 40:
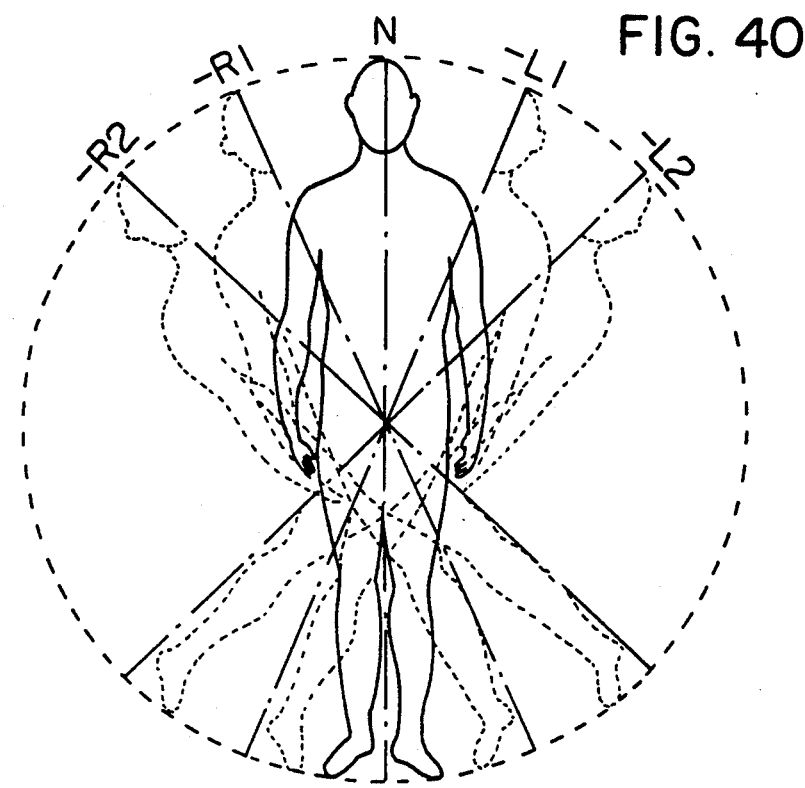
FIGS. 40 and 41 are views of icons displayed in the apparatus of FIG. 33.
Figure 41:
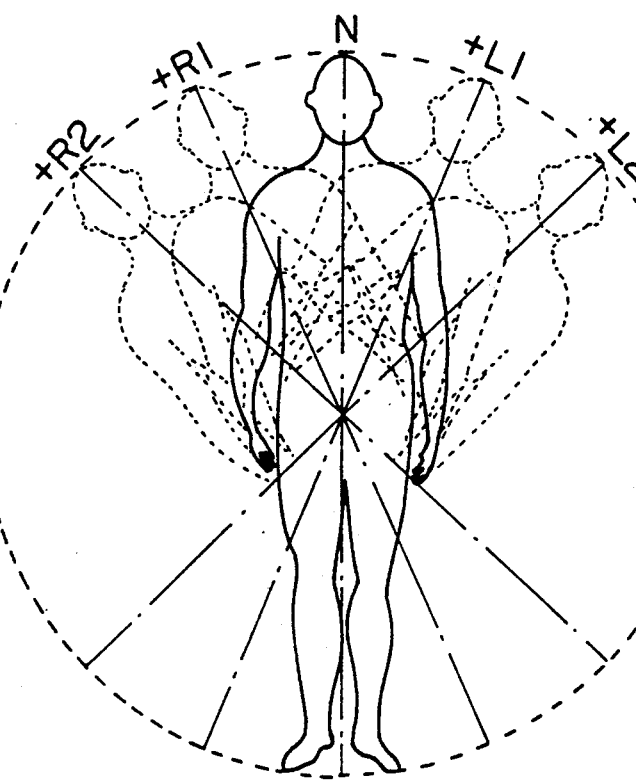
Figure 42:
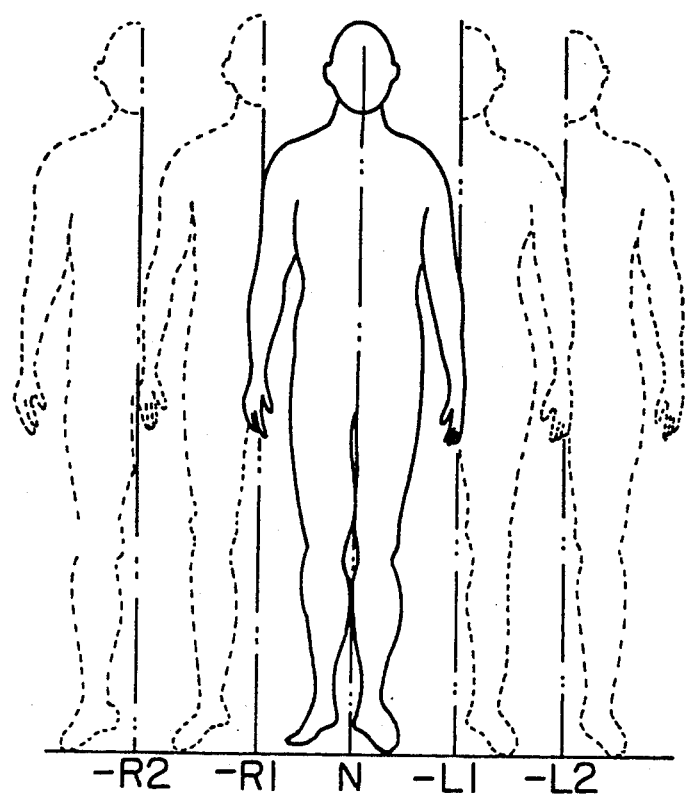
FIG. 42 is a view of icons which may be displayed in the apparatus of FIG. 33.

This pulse-wave/envelopes diagram provides precious data for diagnoses of circulatory diseases. First since the pulse wave W is a pulse wave approximate to an aortic wave as described above, it can non invasively provide circulation information of an approximate aortic wave. The first envelope E1 is the so called swan shaped shape data, which has been conventionally used for the blood pressure diagnosis. Based on this shape, various diagnoses can be made. For example, the various hatched shapes in FIG. 39 are those (whose half sides are shown) defined by the first envelope E1. Shape a is of the standard normal person. Shape b is of the case K5 sound frequently occurs. Shape c is of the case K3 sound and its followers are missed. In some cases, a trapezoid, as of Shape d, and a double peak shape, as of Shape e, are formed. In Shape f, arhythmias are found. In Shape g, insufficient stroke volumes are found. On the other hand, the second envelope E2 presents levels of circulatory diseases at parts they have taken place, which will be descried later in connection with icons/blood circulation trouble part. 5.4 Icons/Blood Circulation Trouble Part Display When a pulse-wave/envelopes diagram is obtained, a icons/blood circulation trouble part display can be obtained based on the pulse-wave/envelopes diagram. This display comprises an icon indication and a circulation trouble part display. The icon indication is a display by means of three icons of the human body. These icons are shown in FIGS. 40 and 41. In FIGS. 40 and 41. N indicates a first icon (in the solid line) which is an upstanding human body indicating a reference position. A second icon indicates a condition of the right half body and is indicated by N, −R1, −R2, +R1, +R2 in FIGS. 40 and 41 (depicted in the broken lines except N). A third icon indicates a condition of the left half body and is indicated by N, −L1, −L2, +L1, +L2 (depicted in the broken lines except N). Which icons are taken as the second and the third icons is determined by a pulse wave/envelopes diagrams of FIG. 38. That is, it is decided depending on which sections of the horizontal axis the peaks S2R and S2L of the second envelope E2 are located in. For example, when the peak S2R is in Section R0, it is judged normal, and icon N is taken as the second icon (which becomes the same as the first icon). When the peak S2R is in Section −R1, −R2, +R1, or +R2, icons −R1, −R2, +R1, +R2 are respectively taken (which are slanted away from the first icon). This procedure is the same with the third icon.

In short, when the peaks S2R, S2L are positioned in the standard Sections R0, L0, the three icons are superposed on one another with the upright human body alone is displayed, but the peaks are outside the standard sections, icons accordingly slanted to the right and the left are displayed. This indicates which one of the left and the right sides and how serious blood circulation trouble is present. A larger inclination of an icon indicates a more serious circulation trouble. When the peaks S2R, S2L are deviated to the negative direction, as shown in FIG. 40, the right and the left half bodies as the icons are displayed. When the peaks S2R, S2L are deviated to the positive direction, as shown in FIG. 41, the upper half of the body is displayed as an icon. Accordingly it is possible to recognize at sight the information whether the peaks are deviated to the side of smaller amplitude Korotkoff sounds or to the side of larger amplitude Korotkoff sounds. In place of the indication of the degree of a circulation trouble by slanting the icons of the human body as shown in FIGS. 40 and 41, it is possible to parallelly move the human bodies to indicate the degree of a circulation trouble. In addition to these method, other various methods can be considered. In place of the human body, more simplified patterns may be used. For example, simple lines may be used. In short, any method may be used as long as it is possible that the second and the third icons are indicative of the degrees of circulation troubles in the right and the left half bodies.

Figure 43:
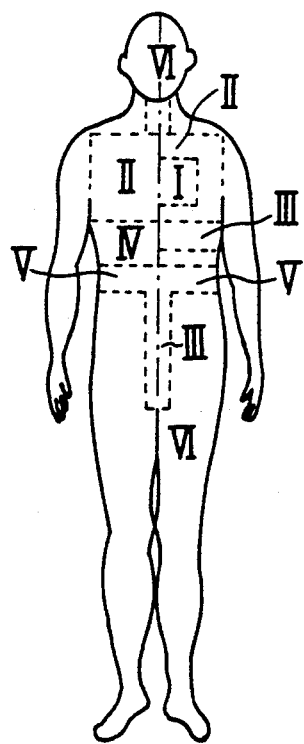
FIG. 43 is a view of blood circulation trouble parts displayed by the apparatus of FIG. 33.
Figure 44:
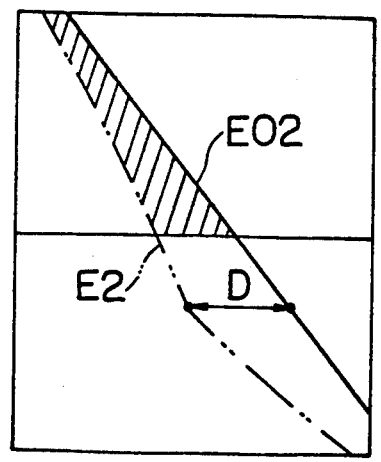
FIG. 44 is a view of one example of methods for judging a blood circulation trouble part by the apparatus of FIG. 33.

Next, circulation trouble part display will be explained. The above described icons display provides information which of the left and the right side of a body has a circulation trouble. The circulation trouble part display specifically indicates which part of the body the circulation trouble has taken place. Now FIG. 38 will be again referred to. As described in §4, a Korotkoff sound waveform indicates circulation trouble information of the vicinity of the heart in Section I, that of the lung in Section II, that of the stomach and the gastrointestines (digestive organs) in Section III, that of the liver in Section IV, that of the kidney in Section V, and that of the bladder, legs and head in Section VI. When these information are represented by the human body icons, they are as shown in FIG. 43. The inventor of the present application has empirically recognized that the second envelope can be the data which is most conspicuously indicative of these circulatory disease information. Then, the second envelope E2 is compared with the corresponding standard envelope E02 in the respective Sections I to VI, and if an interval between the two envelopes E2 and E02 exceeds a set limit in a section, it is judged that a circulatory disease is present in the section. Here, as methods for determing an interval between the envelopes, it may be judged as shown in the upper part of FIG. 44, for example, whether or not the area of a region enclosed by both envelopes exceeds a set value, or it may be judged whether or not a largest interval D exceeds a set value as shown in the lower part of FIG. 44.

In Section VI, it may be judged whether or not a pressure value at which a Korotkoff sound dies out is in a set range. In this embodiment, when an interval between a Korotkoff sound extinguishing pressure (a pressure at Point H in FIGS. 5a and 16a) and a diastolic pressure DP exceeds 10 mmHg, it is judged that a circulatory disease is present in the bladder, legs or head.

Thus, if there is a section among Sections I to VI where the interval exceeds a limit, the part corresponding to the section is displayed as a circulation trouble part. This display is made on the first icon. That is, the part corresponding to a section where it is judged there is a circulation trouble is displayed by specific means (e.g., hatching) on the first human body icon with reference to the positions of the respective parts shown in FIG. 43. Of course it is possible to display a circulation trouble part in letters, but it is preferable that the display is made on the human body icon to facilitate the recognition.

As described above, when the peaks S2R, S2L of the second envelope are in the standard Sections R0, L0, the upstanding human body icon alone is displayed. But in this apparatus, even with the peaks in Sections R0, L0, when a circulatory disease is detected in any of the sections, the human body icon is slanted right or left to Position L1 or R1 corresponding to a part of the detected circulatory disease. Accordingly when a circulation trouble part indication appears at a place, even with the peaks S2R, S2L of the second envelope in the standard Sections R0, L0, a slanted human body icon is displayed without failure.

5.5 Actual Examples of the Display

Figure 45:
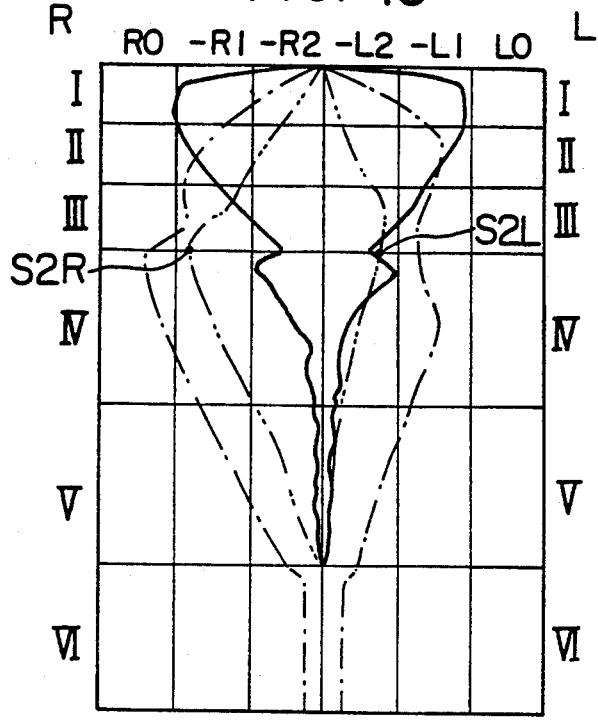
FIG. 45 is a view of one example of pulse wave/envelopes diagrams displayed by the apparatus of FIG. 33.
Figure 46:
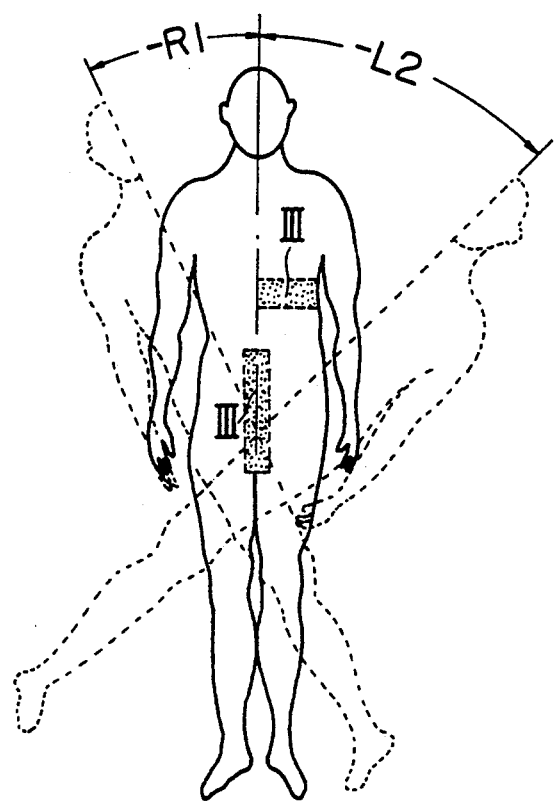
FIG. 46 is a view of an icons/blood circulation trouble part display obtained from the diagram of FIG. 45.

FIG. 45 shows an example of the pulse-wave/envelopes diagrams displayed by this circulation information display apparatus. FIG. 46 is a view of the icons/circulation trouble part display derived from the diagram of FIG. 45. Actually it is preferable to output the chart of FIG. 45 side by side with that of FIG. 46. In FIG. 45, the peaks S2R, S2L are respectively in sections −R1 and Section −L2. In FIG. 46, the right half body is slanted by −R1, and the left half is slanted by −L2. In Section III, the second envelope is deviated from the standard envelope by more than a set limit. In FIG. 46 a circulatory disease part display is made in the gastrointestines (digestive organs) corresponding to Section III.

Figure 47:
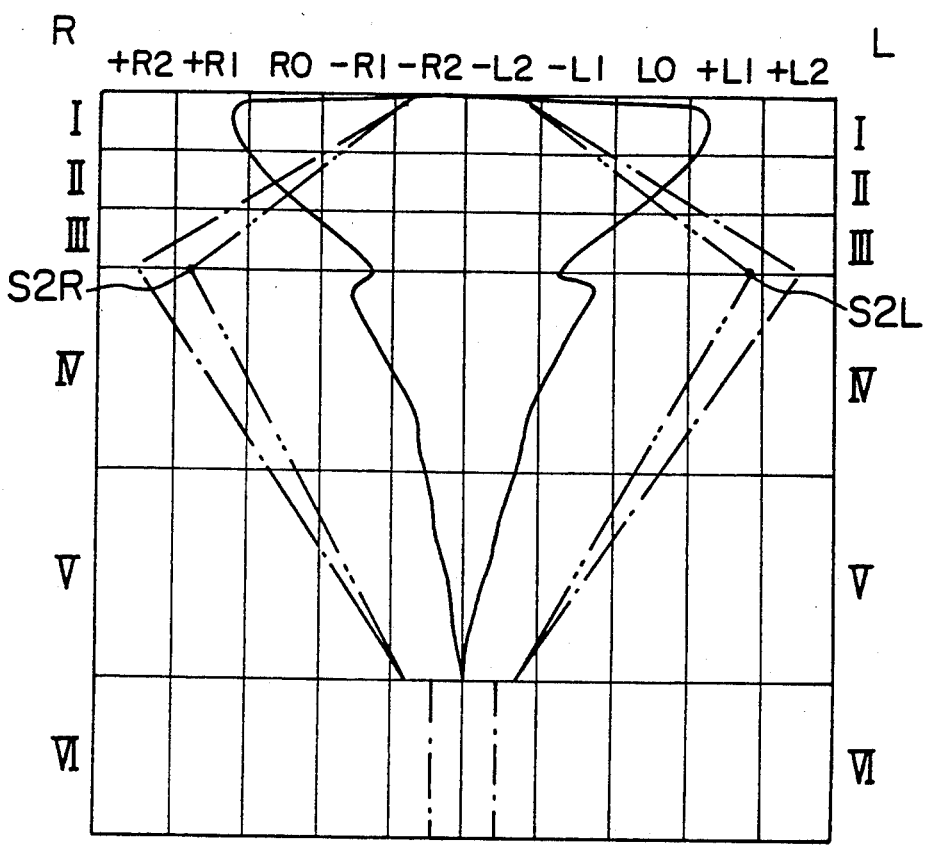
FIG. 47 is a view of another example of pulse wave-/envelopes diagrams displayed by the apparatus of FIG. 33.
Figure 48:
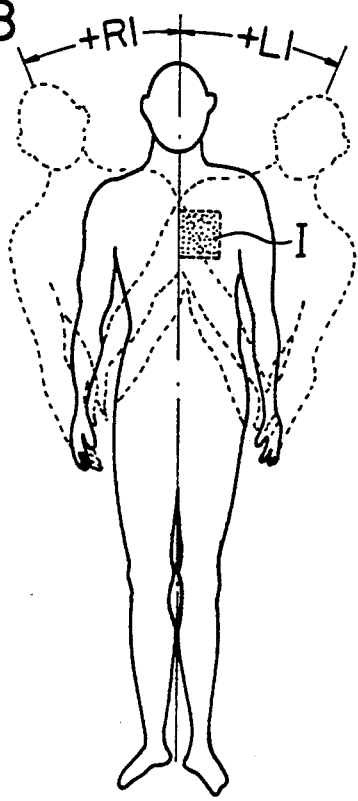
FIG. 48 is a view of an icons/blood circulation trouble part display obtained from the diagram of FIG. 47.

FIG. 47 shows another example of pulse-wave/envelopes diagrams displayed by this circulation information display apparatus. FIG. 48 is a view of the icons/circulation trouble part display derived from the diagram of FIG. 47. In FIG. 47, the peaks S2R, S2L of the second envelope are respectively in Section +R1 and Section +L1. In FIG. 48, the right upper half body is slanted by +R1, and the left upper half body is slanted by +L1. On the other hand, the interval of the second envelope from the standard envelope is within a set limit in the respective sections. Accordingly no conspicuous circulation troubles are found in any of the Sections I to V. But the peaks S2R, S2L of the envelope are present respectively in Sections +R1 and +L1, and pulse waves of larger amplitudes, and larger Korotkoff sounds than those of normal people are detected. In this case, according to this apparatus, it is judged that there are circulation troubles due to abnormally swift palpitation, and as shown in FIG. 48, a circulation trouble part indication is displayed in a part (corresponding to the heart) corresponding to Section I.

Thus, according to a first characteristic of this apparatus, blood pressure values are taken on the vertical axis, time being taken on the horizontal axis, and pulse waves and the two envelopes are compositely displayed on the same time axis. Consequently information for diagnoses of circulatory diseases can be visually seen with ease.

According to a second characteristic of this apparatus, three human body icons are displayed. Consequently, based on locations of the icons, levels of circulatory diseases on the right and the left halves of a body can be visually seen with ease.

According to a third characteristic of this apparatus, an envelope of Korotkoff sound waveform envelope, and a standard envelope are compared, and when an interval between the two exceed a set limit, it is judged that there is a circulatory disease. Consequently it is possible to display a specific part of a detected circulatory disease.

INDUSTRIAL APPLICABILITY

The pulse wave detecting apparatus, the pulse wave changes detecting apparatus, the pulse-wave/arterial sound composite recording apparatus, and the blood circulatory information display apparatus can be used for the diagnosis of circulation diseases. Especially these apparatus can provide measurement results only by putting the cuff(s) on an upper arm (upper arms). Consequently compared with the conventional invasive measuring methods, they have more usefulness. This invention is believed to contribute much to the present medical diagnostic technology.

I claim:

1. An aortic pulse wave detecting apparatus comprising:
   a cuff including a top portion having a blood flow shutting bag for shutting blood flow of an upper arm, and a lower portion including a detection bag for detecting a pulse which has cleared the blood flow shutting bag, wherein both a said bags are located side by side on said cuff for being wound at a position on the upper arm so that the blood flow shutting bag is located at an upstream position and the detection bag is located at a downstream position with respect to an artery;

pressure detecting means for detecting a pressure change in the detection bag generated by a collision of said pulse with said detector bag;

pressure control means for maintaining a reference internal pressure of the blood flow shutting bag and of the detection bag at a set value; and pulse wave output means for providing an output signal representative of, an aortic pulse wave, a pressure change provided by said pressure detecting means while the reference internal pressure is being maintained.

2. An aortic pulse wave detecting apparatus comprising:

a cuff including a top portion having a blood flow shutting bag for shutting blood flow of an upper arm, and a lower portion including a detection bag for detecting a pulse which has cleared the blood flow shutting bag, wherein both a said bags are located side by side on said cuff for being wound at a position on the upper arm so that the blood flow shutting bag is located at an upstream position and the detection bag is located at a downstream position with respect to an artery, sound detecting means for detecting a Korotkoff sound generated under the cuff;

pressure detecting means for detecting a pressure change in the detection bag generated by a collision of said pulse with said detection bag;

pressure control means for maintaining a reference internal pressure of the blood flow shutting bag and of the detection bag at a particular value which is obtained when an amplitude of the Korotkoff sound detected by said sound detecting means becomes a set value; and pulse wave output means for providing an output signal representative of an aortic pulse wave, a pressure change provided by said pressure detecting means while the reference internal pressure is being maintained.

3. An aortic pulse wave detecting apparatus according to claim 2, wherein the pressure control means further comprises:

means for increasing the reference internal pressure to a high pressure value sufficient for shutting a blood flow;

means for gradually decreasing the reference internal pressure from said high pressure value;

means for maintaining the reference internal pressure, for a predetermined period, at the particular value when an amplitude of the Korotkoff sound detected by said sound detecting means becomes a set value, and means for decreasing the reference internal pressure from the particular value to a low pressure value sufficient for taking the cuff off the upper arm.

4. An aortic pulse wave detecting apparatus according to claim 2, wherein the pressure control means further comprises:

means for increasing the reference internal pressure to a high pressure value sufficient for shutting a blood flow;

means for gradually decreasing the reference internal pressure from said high pressure value;

means for increasing the reference internal pressure after when an amplitude of the Korotkoff sound does not change for a predetermined number of beats;

means for maintaining the reference internal pressure at said particular value for a predetermined period when an amplitude of the Korotkoff sound increases by a predetermined amount and means for decreasing the reference internal pressure from the particular value to a low pressure value sufficient for taking the cuff of the upper arm.

* * * * *